US011273235B2

(12) United States Patent
Hadamitzky et al.

(10) Patent No.: US 11,273,235 B2
(45) Date of Patent: Mar. 15, 2022

(54) METHOD AND DEVICE FOR LYMPHEDEMA TREATMENT

(71) Applicant: Fibralign Corporation, Union City, CA (US)

(72) Inventors: Catarina Hadamitzky, Hanover (DE); Tatiana Zaitseva, San Jose, CA (US); Michael V. Paukshto, Foster City, CA (US)

(73) Assignee: Fibralign Corporation, Union City, CA (US)

( * ) Notice: Subject to any disclaimer, the term of this patent is extended or adjusted under 35 U.S.C. 154(b) by 300 days.

(21) Appl. No.: 15/028,391

(22) PCT Filed: Oct. 10, 2014

(86) PCT No.: PCT/US2014/060164
§ 371 (c)(1),
(2) Date: Apr. 8, 2016

(87) PCT Pub. No.: WO2015/054654
PCT Pub. Date: Apr. 16, 2015

(65) Prior Publication Data
US 2016/0256605 A1    Sep. 8, 2016

Related U.S. Application Data

(60) Provisional application No. 61/889,526, filed on Oct. 10, 2013.

(51) Int. Cl.
*A61L 27/24*    (2006.01)
*A61L 27/54*    (2006.01)
(Continued)

(52) U.S. Cl.
CPC .............. *A61L 27/24* (2013.01); *A61B 18/20* (2013.01); *A61F 2/105* (2013.01); *A61K 35/16* (2013.01);
(Continued)

(58) Field of Classification Search
CPC .... A61L 27/3604; A61L 27/507; A61L 27/24; A61L 27/3641; A61M 5/14212;
(Continued)

(56) References Cited

U.S. PATENT DOCUMENTS 4,816,028 A    3/1989 Kapadia et al.
5,171,273 A    12/1992 Silver et al.
(Continued)

FOREIGN PATENT DOCUMENTS

WO    WO 99/047188    9/1999
WO    WO 00/61045 A1    10/2000
(Continued)

OTHER PUBLICATIONS

Yan et al. "Mechanisms of Lymphatic Regeneration after Tissue Transfer." PLoS ONE, vol. 6, No. 2, 2011.*
(Continued)

*Primary Examiner* — William H Matthews
(74) *Attorney, Agent, or Firm* — DLA Piper LLP (US)

(57) ABSTRACT

Materials and methods are provided to direct the formation of new lymphatics and to reconnect the disrupted lymphatic network. These materials and methods enable to improve survival of lymph nodes and lymph node fragments and their integration into a lymphatic network, following lymph node and lymph node fragments transplantation. The treatment or prevention of lymphedema is also addressed. In certain embodiments, a bundle of fibers or fibrils presented in the composition is effective to stimulate and direct the formation of new lymphatic and blood vessels. The bundle of fibers or
(Continued)

fibrils presented in the composition is effective to promote survival of the lymph node or lymph node fragments and integration of the lymph node or lymph node fragments into a lymphatic network in the mammalian subject, at the site of transfer or transplantation.

16 Claims, 18 Drawing Sheets

(51) Int. Cl.
<table>
<tr><td>A61L 27/58</td><td>(2006.01)</td></tr>
<tr><td>A61L 27/60</td><td>(2006.01)</td></tr>
<tr><td>A61K 38/18</td><td>(2006.01)</td></tr>
<tr><td>A61K 35/26</td><td>(2015.01)</td></tr>
<tr><td>A61K 35/16</td><td>(2015.01)</td></tr>
<tr><td>A61B 18/20</td><td>(2006.01)</td></tr>
<tr><td>A61F 2/10</td><td>(2006.01)</td></tr>
<tr><td>A61L 27/36</td><td>(2006.01)</td></tr>
<tr><td>A61L 27/50</td><td>(2006.01)</td></tr>
<tr><td>A61M 5/142</td><td>(2006.01)</td></tr>
<tr><td>A61M 25/01</td><td>(2006.01)</td></tr>
<tr><td>A61M 27/00</td><td>(2006.01)</td></tr>
</table>

(52) U.S. Cl.
CPC .............. *A61K 35/26* (2013.01); *A61K 38/18* (2013.01); *A61L 27/3604* (2013.01); *A61L 27/3641* (2013.01); *A61L 27/507* (2013.01); *A61L 27/54* (2013.01); *A61L 27/58* (2013.01); *A61L 27/60* (2013.01); *A61M 5/14212* (2013.01); *A61M 25/0194* (2013.01); *A61M 27/002* (2013.01); *A61L 2300/104* (2013.01); *A61L 2300/25* (2013.01); *A61L 2300/414* (2013.01); *A61L 2300/604* (2013.01); *A61L 2430/34* (2013.01); *A61M 2025/0197* (2013.01)

(58) Field of Classification Search
CPC ...... A61M 27/002; A61F 2/105; A61K 35/16; A61K 35/26; A61K 38/18
See application file for complete search history.

(56) References Cited

U.S. PATENT DOCUMENTS

<table>
<tr><td>5,378,469 A</td><td>1/1995</td><td>Kemp et al.</td></tr>
<tr><td>5,968,546 A</td><td>10/1999</td><td>Baur et al.</td></tr>
<tr><td>6,544,762 B1</td><td>4/2003</td><td>Tranquillo et al.</td></tr>
<tr><td>6,592,623 B1</td><td>7/2003</td><td>Bowlin et al.</td></tr>
<tr><td>6,887,488 B2</td><td>5/2005</td><td>Cui et al.</td></tr>
<tr><td>7,048,963 B2</td><td>5/2006</td><td>Braithwaite et al.</td></tr>
<tr><td>7,338,517 B2</td><td>3/2008</td><td>Yost et al.</td></tr>
<tr><td>7,648,471 B2</td><td>1/2010</td><td>Hobson</td></tr>
<tr><td>7,744,914 B2</td><td>6/2010</td><td>Li et al.</td></tr>
<tr><td>8,028,647 B2</td><td>10/2011</td><td>McMurtry et al.</td></tr>
<tr><td>8,227,574 B2</td><td>7/2012</td><td>Paukshto et al.</td></tr>
<tr><td>8,513,382 B2</td><td>8/2013</td><td>Paukshto et al.</td></tr>
<tr><td>9,724,308 B2</td><td>8/2017</td><td>Paukshto et al.</td></tr>
<tr><td>2002/0090725 A1</td><td>7/2002</td><td>Simpson et al.</td></tr>
<tr><td>2003/0093107 A1</td><td>5/2003</td><td>Parsonage et al.</td></tr>
<tr><td>2006/0085063 A1</td><td>4/2006</td><td>Shastri et al.</td></tr>
<tr><td>2006/0198827 A1</td><td>9/2006</td><td>Levenberg</td></tr>
<tr><td>2006/0228339 A1</td><td>10/2006</td><td>Wang</td></tr>
<tr><td>2007/0041952 A1</td><td>2/2007</td><td>Guilak et al.</td></tr>
<tr><td>2008/0147199 A1</td><td>6/2008</td><td>Yost et al.</td></tr>
<tr><td>2009/0069893 A1</td><td>3/2009</td><td>Paukshto et al.</td></tr>
<tr><td>2009/0104159 A1</td><td>4/2009</td><td>Prosper et al.</td></tr>
<tr><td>2009/0280180 A1</td><td>11/2009</td><td>Voytik-Harbin et al.</td></tr>
<tr><td>2010/0021520 A1</td><td>1/2010</td><td>Baskin et al.</td></tr>
<tr><td>2010/0036098 A1*</td><td>2/2010</td><td>Paukshto ................ A61L 27/48<br>530/356</td></tr>
<tr><td>2011/0151563 A1</td><td>6/2011</td><td>Paukshto et al.</td></tr>
<tr><td>2011/0206646 A1</td><td>8/2011</td><td>Alfonso et al.</td></tr>
<tr><td>2012/0065703 A1</td><td>3/2012</td><td>Paukshto et al.</td></tr>
<tr><td>2012/0125348 A1</td><td>5/2012</td><td>Alitalo et al.</td></tr>
<tr><td>2013/0287744 A1</td><td>10/2013</td><td>Paukshto et al.</td></tr>
<tr><td>2014/0081070 A1</td><td>3/2014</td><td>Paukshto et al.</td></tr>
<tr><td>2014/0242347 A1</td><td>8/2014</td><td>Paukshto et al.</td></tr>
</table>

FOREIGN PATENT DOCUMENTS

<table>
<tr><td>WO</td><td>WO 2003/020316 A1</td><td>3/2003</td></tr>
<tr><td>WO</td><td>WO 2004/050134 A2</td><td>6/2004</td></tr>
<tr><td>WO</td><td>WO 2005/003300 A2</td><td>1/2005</td></tr>
<tr><td>WO</td><td>WO 2005/081699 A2</td><td>9/2005</td></tr>
<tr><td>WO</td><td>WO 2006/136817 A1</td><td>12/2006</td></tr>
<tr><td>WO</td><td>WO 2007/028078 A2</td><td>3/2007</td></tr>
<tr><td>WO</td><td>WO 2007/038601 A2</td><td>4/2007</td></tr>
<tr><td>WO</td><td>WO 2008/034854 A1</td><td>3/2008</td></tr>
<tr><td>WO</td><td>WO 2008/063631 A2</td><td>5/2008</td></tr>
<tr><td>WO</td><td>WO 2008/070166 A1</td><td>6/2008</td></tr>
<tr><td>WO</td><td>WO 2008/131293 A2</td><td>10/2008</td></tr>
<tr><td>WO</td><td>WO 2009/064437 A1</td><td>5/2009</td></tr>
<tr><td>WO</td><td>WO 2011/028579 A2</td><td>3/2011</td></tr>
<tr><td>WO</td><td>2012/034110 A2</td><td>3/2012</td></tr>
<tr><td>WO</td><td>2013/103423 A2</td><td>7/2013</td></tr>
<tr><td>WO</td><td>2014/018685 A1</td><td>1/2014</td></tr>
<tr><td>WO</td><td>WO 2015/054654 A1</td><td>4/2015</td></tr>
</table>

OTHER PUBLICATIONS

International Search Report and Written Opinion for International Application No. PCT/US2014/060164, dated Mar. 12, 2015.
Notice of Allowance in U.S. Appl. No. 14/351,128, dated Nov. 6, 2018.
Besseau, L. et al., "Production of Ordered Collagen Matrices for Three-Dimensional Cell Culture," Biomaterials, 23, 2002, pp. 27-36.
Besseau, Laurence et al., "Stabilization Of Fluid Cholesteric Phases Of Collagen To Ordered Gelated Matrices", Journal of Molecular Biology, vol. 251, pp. 197-202, Aug. 1995.
Boardman et al., "Interstitial Flow As A Guide For Lymphangiogenesis", Circulation Research, vol. 92, No. 7, pp. 801-808, published online Mar. 2003.
Cisneros, D. et al., "Creating Ultrathin Nanoscopic Collagen Matrices for Biological and Biotechnological Applications", Wiley InterScience, 2007, vol. 3, No. 6, pp. 956-963.
Eglin, D. et al., "Type I Collagen, a Versatile Liquid Crystal Biological Template for Silica Structuration from Nano-to Microscopic Scales," The Royal Society of Chemistry, vol. 1, 2005, pp. 129-131.
Evans, H., et al. "Novel 3D Culture System for Study of Cardiac Myocyte Development," Am J. Physiol Heart Circ Physiol, vol. 285, 2003, pp. H570-H578.
Freed, A.D. et al., "Elastic Model for Crimped Collagen Fibril," Journal of Biomechanical Engineering, Aug. 2005, vol. 127, pp. 587-593.
Gobeaux, F., "Cooperative Ordering of Collagen Triple Helices in the Dense State", Langmuir 2007, vol. 23, pp. 6411-6417.
Gobeaux, F. et al., "Fibrillogenesis In Dense Collagen Solutions: A Physicochemical Study", Journal of Molecular Biology, vol. 376, pp. 1509-1522, Mar. 2008.
Guo, C. et al., "Flow and Magnetic Field Induced Collagen Alignment," Biomaterials, vol. 28, 2007, pp. 1105-1114.
Hibino et al., "A Critical Role For Macrophages In Neovessel Formation And The Development Of Stenosis In Tissue-Engineered Vascular Grafts", The FASEB Jounal, Dec. 2011 (published online Aug. 2011), vol. 25, No. 12, pp. 4253-4263.
Huang et al., "The Modulation Of Endothelial Cell Morphology, Function, And Survival Using Anisotropic Nanofibrillar Collagen Scaffolds", Biomaterials, May 2013 (published online Mar. 2013), vol. 34, No. 16, pp. 4038-4047.
Hulmes, David J.S., "Building Collagen Molecules, Fibrils, and Suprafibrillar Structures", Journal of Structural Biology, vol. 137, pp. 2-10, Jan. 2002.

(56) References Cited

OTHER PUBLICATIONS

Jiang, et al., Assembly of collagen into microribbons: effects of pH and electrolytes; Journal of Structural Biology, Academic Press, United States, vol. 148, No. 3, Dec. 1, 2004; pp. 268-278.

Kirkwood, John E. et al., "Liquid Crystalline Collagen: A Self-Assembled Morphology for the Orientation of Mammalian Cells", Langmuir, 2009, vol. 25, pp. 3200-3206, published on web Feb. 10, 2009.

Knight, D. et al. "Biological Liquid Crystal Elastomers," Philosophical Transactions: Biological Sciences, vol. 357, No. 1418, Estomeric Proteins: Structures, Biomechanical Properties and Biological Roles., Feb. 12, 2002, pp. 155-163.

Koster, et al., Visualization of Flow-Aligned Type I Collagen Self-Assembly in Tunable pH Gradients; Langmuir, vol. 23, 2007, pp. 357-359.

Lai, Edwina S. et al., "Aligned Nanofibrillar Collagen Regulates Endothelial Organization and Migration" Regenerative Medicine, vol. 7, No. 5, pp. 649-661, 2012.

Ledet, E. H. et al., "A Pilot Study to Evaluate the Effectiveness of Small Intestinal Submucosa Used to Repair Spinal Ligaments in the Goat," The Spine Journal, vol. 2, No. 3, May-Jun. 2002, pp. 188-196.

Martin, G. R. et al., "Behavior Of Cells on Highly Organized and Reconstituted Collagen Matices," The Cell, Bethesda MS USA, vol. 19, Dec. 13, 2008, p. 42.

Martin, R. et al., "Liquid Crystalline Ordering of Procollagen as a Determinant of Three-Dimensional Extracellular Matrix Architecture," J. Mol. Biol., vol. 301, 2000, pp. 11-17.

Mosser, G., et al., "Dense tissue-like collagen matrices formed in cell-free conditions", Matrix Biology, 2006, 25, pp. 3-13.

Muthusubramaniam, L. et al., "Collagen Fibril Diameter and Alignment Promote the Quiescent Keratocyte Phenotype", J Biomed Mater Res Part A, 100A, (3), 613-621, published online Dec. 2011.

Yoshizato, K. et al., "In Vitro Orientation of Fibroblasts and Myoblasts on Aligned Collagen Film", Develop., Growth and Differ., 23 (2), 1981, pp. 175-184.

Zhong, S. et al., "An Aligned Nanofibrous Collagen Scaffold by Electrospinning and its Effects on In Vitro Fibroblast Culture", Journal of Biomedical Materials Research Part A, 2006 Wiley Periodicals, Inc., pp. 456-463.

International Search Report and Written Opinion in International Application No. PCT/US2012/059830, dated Jul. 25, 2013.

Office Action in U.S. Appl. No. 14/351,128, dated Jul. 28, 2016.

Office Action in U.S. Appl. No. 14/351,128, dated Mar. 30, 2017.

Office Action in U.S. Appl. No. 14/351,128, dated Feb. 8, 2018.

Nesbitt, S., et al., "Collagen Fibrils in Skin Orient in the Direction of Applied Uniaxial Load in Proportion to Stress while Exhibiting Differential Strains around Hair Follicles," Materials (Basel), Apr. 2015, vol. 8, Issue 4, pp. 1841-1857.

\* cited by examiner

Procedure for thread implantation using slider cassette

1. Loading threads into grooves and securing the lid.

2. Inserting the slider cassette into subcutaneous tunnel.

3. Holding the threads in place with a clamp and pulling the slider out of the tunnel.

4. Securing the threads with sutures.

- BioBridge cross-section
- Formation of new vessels along BioBridge

METHOD AND DEVICE FOR LYMPHEDEMA TREATMENT

FIELD OF THE INVENTION

The present invention generally relates to materials and methods to improve healing of skin and underlying tissue following a surgical procedure. Embodiments of the present invention provides materials and methods for repairing tissue, for the reduction of edema, for reconnection of the lymphatic system damaged after trauma, infection, radiation or surgery, and for induction or regeneration of new lymphatics.

RELATED APPLICATIONS

This patent application is a united States National Stage Application filed under 35 U.S.C. § 371 of International Application No. PCT/US2014/060164, entitled "Method And Device For Lymphedema Treatment" which was filed on Oct. 10, 2014 which claims the benefit of, and priority to, U.S. Provisional Patent Application Ser. No. 61/889,526 filed on Oct. 10, 2013, the disclosure of which is hereby incorporated by reference in its entirety.

BACKGROUND

The lymphatic system plays many important roles in bodily tissues including the removal of excess interstitial fluid, high molecular weight proteins, fat absorption in the intestine and the transport of cells, particularly lymphocytes, to lymph nodes (LN) in the generation of immune responses. The lymphatic circulation begins as blind-ended capillaries present in almost every tissue of the body. These lymphatic capillaries absorb protein and fluid that have escaped from the systemic circulation. The capillaries merge to form larger vessels that converge in serial LN chains and eventually terminate in the thoracic duct. On average in a healthy human, the lymphatics return about 4 liter of fluid and 400 g of protein back to the systemic circulation every 24 hours through the thoracic duct, which drains into the left subclavian vein (Cooke J P, Rooke T W. 1996. Lymphedema. In: Loscalzo J, Creager M A, Dzau V J, editors. *Vascular Medicine: A Textbook of Vascular Biology and Diseases* 2nd ed. Boston: Little, Brown and Company. pp. 1133-46; and Rockson S and Cooke J P. 2005. *Diseases of the Lymphatic Circulation. In: "Vascular Medicine: A Companion to Braunwald's Heart Disease‖. Ed*: Creager M A, Dzau V J, Rockson S.). Another 6 liter of fluid are reabsorbed at the level of the lymph node chains into the lymph node venules. The lymphatics also play a critical role in immunity, by acting as a conduit for foreign antigens to reach the lymphatic nodes, where they stimulate an immune response.

When the lymphatics become obstructed, fluid and protein accumulate in the tissue, causing the condition of lymphedema. Lymphedema is associated with both impaired immune function (Beilhack A, Rockson S G. *Immune traffic: a functional overview. Lymphat Res Biol* 2003; 1: 219-234; and Johnson L A, Jackson D G. *Cell traffic and the lymphatic endothelium. Ann N Y Acad Sci* 2008; 1131: 119-133) and a loss of normal cutaneous architecture and function (Rockson S G. *Lymphedema. Am J Med* 2001; 110: 288-295). Chronic lymphedema leads to increased numbers of keratinocytes, fibroblasts, and adipocytes in the affected tissue, suggesting a chronic inflammatory response (Piller N B. *Macrophage and tissue changes in the developmental phases of secondary lymphoedema and during conservative therapy with benzopyrone. Arch Histol Cytol* 1990; 53: 209-218) as well as thickening of the lymphatic vascular basement membrane, and fragmentation and degeneration of elastic fibers (Ryan T, de Berker D. *The interstitium, the connective tissue environment of the lymphatic, and angiogenesis in human skin. Clin Dermatol* 1995; 13: 451-458), and prominent collagen deposition manifesting clinically as cutaneous and subcutaneous fibrosis (Tabibiazar R, Cheung L, Han J, et al. *Inflammatory manifestations of experimental lymphatic insufficiency. PLoS Med* 2006; 3: e254), remodeling of the skin and subcutaneous extracellular matrix (ECM) and accumulation of lipids (Campisi C, Boccardo F: *Lymphedema and microsurgery. Microsurgery* 2002, 22:74-80; Piller N B: *Macrophage and tissue changes in the developmental phases of secondary lymphoedema and during conservative therapy with benzopyrone. Arch Histol Cytol* 1990, 53 Suppl: 209-218; Rutkowski J M Markhus C E. Gyenge C C. Alitalo K. Wiig H. Swartz M A. *Dermal collagen and lipid deposition correlate with tissue swelling and hydraulic conductivity in murine primary lymphedema. American Journal of Pathology.* 176(3):1122-9, 2010; and Schirger A, Harrison E G Jr, Janes J M: *Idiopathic lymphedema. Review of* 131 *cases. JAMA* 1962, 182:14-22). As the lymphatic function is tightly controlled by the mechanical attachment of lymphatic endothelium to the surrounding ECM (Grimaldi A, Moriondo A, Sciacca L, Guidali M L, Tettamanti G, Negrini D: *Functional arrangement of rat diaphragmatic initial lymphatic network. Am J Physiol Heart Circ Physiol* 2006, 291:H876-H885; and Swartz M A: *The physiology of the lymphatic system. Adv Drug Deliv Rev* 2001, 50:3-2014), these structural changes further retard interstitial fluid clearance (Swartz M A, Kaipainen A, Netti P A, Brekken C, Boucher Y, Grodzinsky A J, Jain R K: *Mechanics of interstitial-lymphatic fluid transport: theoretical foundation and experimental validation. J Biomech* 1999, 32:1297-1307).

In the United States and Western countries, the most common causes of secondary lymphedema are LN resection and/or radiation for breast and gynecological cancers in women and prostate cancer in men (Armer J, Fu M R, Wainstock J M, Zagar E, Jacobs L K (2004) *Lymphedema following breast cancer treatment, including sentinel lymph node biopsy. Lymphology* 37: 73-91; Beesley V, Janda M, Eakin E, Obermair A, Battistutta D (2007) *Lymphedema after gynecological cancer treatment: prevalence, correlates, and supportive care needs. Cancer* 109: 2607-2614; and Hayes S C, Janda M, Cornish B, Battistutta D, Newman B (2008) *Lymphedema after breast cancer: incidence, risk factors, and effect on upper body function. J Clin Oncol* 26: 3536-3542). It is estimated that as many as 30% of patients treated with LN dissection go on to develop lymphedema, even after more limited surgeries such as sentinel LN biopsy (Petrek J A, Senie R T, Peters M, Rosen P P (2001) *Lymphedema in a cohort of breast carcinoma survivors 20 years after diagnosis. Cancer* 92: 1368-1377; McLaughlin S A. Wright M J. Morris K T. Giron G L. Sampson M R. Brockway J P. Hurley K E. Riedel E R. Van Zee K J. (2008) *Prevalence of lymphedema in women with breast cancer 5 years after sentinel lymph node biopsy or axillary dissection: objective measurements. J Clin Oncol* 26: 5213-5219; and McLaughlin S A, Wright M J, Morris K T, Sampson M R, Brockway J P, et al. (2008) *Prevalence of lymphedema in women with breast cancer 5 years after sentinel lymph node biopsy or axillary dissection: patient perceptions and precautionary behaviors. J Clin Oncol* 26: 5220-5226). Furthermore, lymphedema results in a nearly $10,000 increase in the two-year treatment cost of breast cancer patients (Shih Y C. Xu Y Cormier J N. Giordano S. Ridner S H. Buchholz T A. Perkins G H. Elting L S. (2009) *Incidence, treatment costs, and complications of lymphedema after breast cancer among women of working age: a 2-year follow-up study. J Clin Oncol* 27: 2007-2014). With over 300,000 new breast cancers diagnosed annually, lymphedema is a significant biomedical burden.

In certain tropical countries, a common cause of lymphedema is a parasitic infection, filariasis. Other causes of secondary lymphedema include trauma from burns, surgery, and physical injuries, and skin infections. Chronic lymphedema is an irreversible, debilitating, and lifelong condition that causes pain and discomfort, disfigurement, skin damage, fibrosis, and limb malfunction. Patients with this complication have a significantly decreased quality of life with frequent infections, decreased range of motion, and a cosmetic deformity that is difficult to conceal (Ahmed R L, Prizment A, Lazovich D, Schmitz K H, Folsom A R (2008) *Lymphedema and quality of life in breast cancer survivors: the Iowa Women's Health Study. J Clin Oncol* 26: 5689-5696), as well as profound, quantifiable impairment of psychosocial adjustment (Velanovich V, Szymanski W. *Quality of life of breast cancer patients with lymphedema. Am J Surg* 1999; 177: 184-187; Person B, Bartholomew L K, Addiss D, van den Borne B. *Disrupted social connectedness among Dominican women with chronic filarial lymphedema. Patient Educ Couns* 2007; 68: 279-286; and McWayne J, Heiney S P. *Psychologic and social sequelaeof secondary lymphedema: a review. Cancer* 2005; 104: 457-466). In addition, breast cancer survivors with lymphedema incur higher medical cost and access mental health services to a significantly greater degree (Shih Y C. Xu Y. Cormier J N. Giordano S. Ridner S H. Buchholz T A. Perkins G H. Elting L S. (2009) *Incidence, treatment costs, and complications of lymphedema after breast cancer among women of working age: a 2-year follow-up study. J Clin Oncol* 27: 2007-2014).

No treatment to date can truly restore tissue fluid balance or improve lymphatic function. The conventional treatment for lymphedema is palliative, and focuses on reducing the swelling and treating infections. The usual treatments include lymphatic drainage and compressive garments to decrease fluid accumulation and encourage drainage of interstitial fluid, but are only partially successful in reducing limb volume, time consuming and do not reverse the basic pathology of lymphedema (Szuba A, Cooke J P, Yousuf S, Rockson S. 2000. *Decongestive lymphatic therapy for patients with cancer-related or primary lymphedema. Am J Med* 109(4): 296-300; and Cooke J P, Szuba A, Rosenbaum E H. 2007. Lymphedema. In: Rosenbaum E H, Spiegel D, Fobair P, Gautier H (eds). *Everyone's Guide to Cancer Therapy: A Roadmap for Better Health.* Kansas City, Mo., Andrews McMeel, pp. 226-229). More importantly, once compression and manual drainage are stopped, lymphedema recurs and in most cases worsens over time. Current surgical treatment options aiming the cure of the lymphatic obstruction are limited to lymphatic anastomoses and healthy tissue transplantation. Lymphatico-venous anastomoses or lymphatico-lymphatic anastomoses remain a challenging technique (Baumeister R G, Frick A. 2003. *The microsurgical lymph vessel transplantation. Handchir. Mikrochir. Plast. Chir.* 35: 202-209; and Campisi, C., Eretta, C., Pertile, D., Da Rin, E., Campisi, C., Maccio, A., Campisi, M., Accogli, S., Bellini, C., Bonioli, E., Boccardo, F., 2007. *Microsurgery for treatment of peripheral lymphedema: long-term outcome and future perspectives. Microsurgery* 27: 333-338). Transplantation of healthy tissues to replace or re-route damaged lymphatic vessels, in which only arterial and venous vessels are reconnected but lymphatic vessels are not re-anastomosed, has shown improvements in lymphedema patients with evidence of lymphatic re-routing (Yan A. Avraham T. Zampell J C. Aschen S Z. Mehrara B J. *Mechanisms of lymphatic regeneration after tissue transfer. PLoS ONE* 2011, 6(2):e17201; and Classen D A, Irvine L (2005) *Free muscle flap transfer as a lymphatic bridge for upper extremity lymphedema. J Reconstr Microsurg* 21: 93-99) and clinical evidence of spontaneous lymphatic regeneration (Anthony J P, Foster R D, Price D C, Mandavian M, Inoue Y (1997) *Lymphatic regeneration following microvascular limb replantation: a qualitative and quantitative animal study. JReconstr Microsurg* 13: 327-330). Although LN transfer has been shown to provide some benefit in human lymphedema patients (Becker C, Assouad J, Riquet M, Hidden G. *Postmastectomy lymphedema: long-term results following microsurgical lymph node transplantation. Ann Surg.* 2006; 243:313-315), autologous LN incorporate into existing lymphatic vasculature at a low rate (22% to 31%) (Becker C, Assouad J, Riquet M, Hidden G. *Postmastectomy lymphedema: long-term results following microsurgical lymph node transplantation. Ann Surg.* 2006; 243:313-315; and Tammela T, Saaristo A, Holopainen T, Lyytikka¨ J, Kotronen A, Pitkonen M, Abo-Ramadan U, Yla¨-Herttuala S, Petrova T V, Alitalo K. *Therapeutic differentiation and maturation of lymphatic vessels after lymph node dissection and transplantation. Nat Med.* 2007; 13:1458-1466), thus compromising the outcome because connection with lymphatic vessels is required for maintenance and function of the LN (Mebius R E, Streeter P R, Breve J, Duijvestijn A M, Kraal G. *The influence of afferent lymphatic vessel interruption on vascular addressin expression. J Cell Biol.* 1991; 115:85-95). In addition, this procedure is lengthy and involves the removal of LN from the donor site, which could predispose the healthy tissue to lymphedema in the future Skin flap survival following surgical procedures, especially reconstructive surgical procedures, is often compromised by, among other complications, infection, ischemia and tissue edema. Tissue and skin flap breakdown remain a major problem in plastic surgery, especially in patients suffering from diabetic microangiopathy or other forms of peripheral vascular disease. In such patients wound healing is often delayed and defective and in these patients complications may lead to necrosis and eventually require costly and painful secondary surgical procedures. However, the modest benefit observed with LN transplantation does provide proof of concept for the approach presented here.

The bundle of the tubular silk threads was successfully used by W. S. Handley (Handley W. S., *The Lancet,* 1908, 171(4411): 783-785) to treat breast cancer related lymphedema. To describe the capillary flow process initiated by the threads he stated that "the operation is closely analogous to the drainage of marshy field by lines of buried pipes". He also noted that after being in the body for 10 years "though eroded at its surface the main substance of the thread is intact. Moreover, leucocytes are evidently unable to penetrate between the fibrils of the silk, for the interior of the thread is entirely free from cellular elements. Nor is there any microscopical indication of the coagulation of the body fluids in the interstices of the silk". Later it was shown (Hartley H. and Harper R. A. K., *Lymphangioplasty—the fate of silk, Br. Med J.,* 1937, 2(4012); 1066-1067) that the silk thread can persist in the soft tissues for twenty four years. Therefore the silk should be considered as a poorly degradable material. Similar experiments were presented in Silver D, Puckett C. *Surgery.* 1976, 80(6): 748-55, where the multifilament Teflon wick was used for the treatment of sixteen patients with refractory primary and secondary lymphedema. There were no operative deaths or operative complications. All patients experienced an early reduction of their edema. The average duration of benefit was 13 months. These two examples demonstrated that the capillary flow of extracellular fluid induced by the threads or multi-filaments can reduce the edema but the beneficial effects are transient. The present invention is intended to preserve the effect of the treatment by creating a suitable extracellular environment in the vicinity of the capillary flow in order to promote a formation of new lymphatic and blood vessels.

The lymphatic vasculature transports fluid and macromolecules from tissues back to the blood circulation and allows for tissue fluid to pass through lymph nodes as an immune surveillance system. Metastatic tumor cells frequently spread via the lymphatic vascular system and are caught by immune cells in the lymph nodes where they are not destroyed as they are identified as belonging to oneself. Breast cancer and melanoma in particular frequently spread to lymph nodes, necessitating radical surgery that destroys lymphatic vessel network and leads to the impairment of afferent lymphatic flow. Approximately 20-30% of patients that have undergone radical axillary lymph node dissection develop lymphedema later on. Lymphedema is a progressive disease characterized by gross swelling of the affected limb, accompanied by fibrosis and susceptibility to infections.

Damage to the collecting lymphatic vessels causes the vast majority of all lymphedemas, and it has been estimated that several million patients suffer from such acquired lymphedema in the United States alone. In contrast, Milroy disease and other rare hereditary forms of lymphedema are caused by defects in lymphatic capillaries. VEGF-C therapy has shown promising efficacy in preclinical animal models. However, this method has only demonstrated lymphatic capillary reconstitution, whereas effects on the collecting lymphatic vessels that are more commonly damaged in lymphedema have not been addressed.

It has been reported that autologous lymph node transfer appears to have a favorable and persistent effect on postmastectomy lymphedema in humans. Lymph node transplantation may be used to treat limb lymphedema with other procurement sites such as cervical or auxiliary being possible.

Lymphatic vasculature plays a key role in the maintenance of tissue fluid homeostasis by collecting and draining extracelullar fluid and macromolecules back to the blood circulation. The lymphatic system also has a major role in immune defense. The lymphatic capillaries in the peripheral tissues merge with larger collecting lymphatic vessels, specialized for the transport of large volumes of lymph, and connect with chains of lymph nodes. Chronic lymphedema, caused commonly by infection and surgical or radiation therapy of metastatic cancer remains a common clinical problem that lacks curative options. The effective treatment and staging of cancer often requires removal of regional lymph nodes and the associated collecting lymphatic vessels to eradicate or prevent metastases. This leads to a disruption in the lymphatic flow of the operated area, which frequently leads to lymphedema of the affected limb. The conventional treatment for chronic lymphedema aims at alleviating the symptoms and is mainly based on physiotherapy and/or controlled compression therapy, whereas surgical treatment options are limited. Recently a microvascular lymph node transfer into axillas of patients that had undergone axillary lymph node dissection in response to disseminated breast cancer was shown to improve lymphatic drainage in some patients.

The lymphatic system is important in tissue fluid balance regulation, immune cell trafficking, edema, and cancer metastasis, yet very little is known about the sequence of events that initiate and coordinate lymphangiogenesis. An in-vivo model of skin regeneration developed in Boardman K C, Swartz M A. *Interstitial flow as a guide for lymphangiogenesis. Circ. Res.* 2003, 92(7):801-8 using a collagen implant in a mouse tail shows that (1) interstitial fluid channels form before lymphatic endothelial cell organization and (2) lymphatic cell migration, vascular endothelial growth factor expression, and lymphatic capillary network organization are initiated primarily in the direction of lymph flow. These data suggest that interstitial fluid channeling precedes and may even direct lymphangiogenesis. Therefore the initial capillary flow developed by a composition comprising a bundle of threads or multi-filaments or fibers or fibrils may initiate the formation of lymphatic vasculature if the composition support cell migration and provide a suitable micro-environment for endothelial cells. The graft consisting of a biodegradable polyglycolic or polylactic acid scaffold may create such micro-environment as it has been shown in Hibino N, Yi T, Duncan D R, Rathore A, Dean E, Naito J, Dardik A, Kyriakides T, Madri J, Pober J S, Shinoka T, Breuer C K., *A critical role for macrophages in neovessel formation and the development of stenosis in tissue-engineered vascular grafts. FASEB J.* 2011, 25: 4253-4263. The biodegradable polyglycolic or polylactic acid scaffolds can be made by electrospinning. Moreover this method can produce aligned fibers and is applicable to many other biodegradable biopolymers. Another promising material is the collagen or the combination of the collagen with other biocompatible and biodegradable biopolymer. A thread-like scaffold or bundle of pseudo-fibers prepared according to U.S. Pat. No. 8,513,382 provide a suitable micro-environment for endothelial cells (Huang N F, Okogbaa J N, Lee J C, Paukshto M, Zaitseva T, Cooke J P. *The Modulation of Endothelial Cell Morphology, Function, and Survival Using Anisotropic Nanofibrillar Collagen Scaffolds. Biomaterials,* 2013, 34: 4038-4047). In particular, they preserve microvascular endothelial cell phenotype and guide cell migration along the aligned collagen fibrils. While some advancements have been made, there is significant need for the development of new lymphedema treatments.

BRIEF SUMMARY

The present invention addresses the unmet needs in the field of medicine by providing materials and methods to generate and direct the formation of new vasculature including lymphatic capillaries and lymphatic collectors, improve survival of lymph nodes and lymph node fragments and their integration into a lymphatic system, combined with lymph node or lymph node fragment transplantation. The use of these methods for preventative treatment of lymphedema is also addressed.

Embodiments of the present invention provide a novel approach to lymphangioplasty which combines the formation of a capillary flow in the body from the area of edema to a healthy part and following regeneration of vasculature in the direction of the flow. In one embodiment, the composition used to induce the capillary flow and to direct the formation of new vasculature comprises a bundle of threads or multi-filaments or fibers or fibrils made from biocompatible and biodegradable materials. In addition, the composition may comprise lymph node fragments and/or growth factors. In certain embodiments, the composition promotes survival of the lymph node or lymph node fragment and their integration into a lymphatic network in the mammalian subject, at the site of transfer or transplantation. It reconnects the healthy lymphatics with transferred or transplanted lymph node or lymph node fragment. The bundle provides the effective bridge between healthy lymphatics and transferred or transplanted lymph node or lymph node fragment and directs lymphatic and vascular regeneration along the bundle. In some embodiments the bundle is connected or attached to healthy lymphatics by one end and to transferred or transplanted lymph node or lymph node fragment by other end. In some embodiments the bundle is attached in the close proximity of healthy lymphatics and transferred or transplanted lymph node or lymph node fragment.

"Transferring or transplanting a lymph node or lymph node fragment" refers to either transferring or transplanting an isolated lymph node or fragment, or transferring or transplanting tissue that contains the lymph node or fragment.

Embodiments of the present invention provides the use of biocompatible and biodegradable materials selected from the group consisting of collagen, fibronectin, fibrin, laminin, elastin, hyaluronic acid, chitosan, silk, peptides, biodegradable block copolymers, lactide and glycolide polymers, caprolactone polymers, hydroxybutyric acids, polyanhydrides and polyesters, polyphosphazenes, polyphosphoesters, poly(ethylene glycol) (PEG) and poly(ethylene oxide) (PEO) including PEG and PEO with different end-functionalities, as well as bifunctional cross-linkers and crosslinking agents. The combinations of the above materials can also be used for the manufacturing of a bundle of threads or multi-filaments or fibers or fibrils.

In yet another embodiment, the invention provides a method of treating or inhibiting lymphedema in a mammalian subject comprising performing a lymph node transfer procedure on a mammalian that comprises transferring or transplanting a lymph node or lymph node fragment in the mammalian subject to a site at which the subject is experiencing lymphedema, or is at risk for lymphedema and, in addition, bridging a perinodal space by a composition comprising a bundle of threads or multi-filaments or fibers or fibrils made from biocompatible and biodegradable materials. In some preferred embodiments, the lymphedema is secondary lymphedema. "Secondary lymphedema" means a lymphedema caused by inflammatory or neoplastic obstruction of lymphatic vessels, and includes without limitation accumulation of ascites fluid due to peritoneal carcinomatosis or edema of the arm or other limbs following surgery or radiotherapy for breast cancer and other tumor types. Secondary lymphedema may also result from a trauma, a crush injury, hip or knee surgery, amputations, blood clots, vein grafts from cardiac surgery, chronic infections, or longstanding circulatory problems such as chronic venous insufficiency or diabetes. Secondary lymphedema may also be idiopathic in origin. The use of a composition described herein for the treatment of secondary lymphedema caused by any of the foregoing disorders is specifically contemplated.

In a preferred embodiment, the mammalian subject is human.

In some embodiments, the present invention involves transferring or transplanting at least one whole lymph node or lymph node fragment. In some variations, the lymph node or lymph node fragment is allogeneic transplant. In another variation, the lymph node is autologously transferred or transplanted from one location in the subject to another location in the same subject.

Optionally, the composition further comprises growth factors, such as for example and without limitation, Vascular Endothelial Growth Factors (VEGFs) or Hepatocyte Growth Factors (HGFs) or cells attached or encapsulated in the bundle of threads or multi-filaments or fibers or fibrils made from biocompatible and biodegradable materials in an amount effective to stimulate vascular and/or lymphatic regeneration in the specific area and to reduce edema or increase perfusion at the skin graft or skin flap, thereby improving the healing of the skin graft or skin flap.

The improvements to surgical skin graft/skin flap procedures (or to isolated tissue containing a lymph node or a lymph node fragment) described herein are applicable to a wide variety of surgeries. For example, in one variation, the underlying tissue is breast tissue. In a preferred embodiment, the skin graft or skin flap is attached in a breast augmentation, breast reduction, mastopexy, or gynecomastia treatment procedure.

In one embodiment, the surgery is a cosmetic surgery procedure. In a preferred embodiment, the cosmetic surgery is a facial cosmetic surgery procedure selected from the group consisting of rhytidectomy, browlift, otoplasty, blepharoplasty, rhinoplasty, facial implant, and hair replacement therapy. In another embodiment, the surgery is a reconstructive surgery. In other embodiment, the reconstructive surgery corrects a congenital defect selected from the group consisting of birthmark, cleft palate, cleft lip, syndactyly, urogenital and anorectal malformations, craniofacial birth defects, ear and nasal deformities, and vaginal agenesis. In some other embodiment, the reconstructive surgery corrects a defect from an injury, infection, or disease. In yet another preferred embodiment, the reconstructive surgery corrects damage from a burn or skin cancer (or skin cancer related treatment). In another embodiment, the reconstructive surgery is breast reconstruction following mastectomy or injury.

In another embodiment, the present invention provides a method of improving the healing of a skin graft or skin flap to underlying tissue of a mammalian subject, comprising contacting skin graft or skin flap tissue or underlying tissue with a composition comprising growth factors such as Vascular Endothelial Growth Factors or Hepatocyte Growth Factors or cells attached or encapsulated in the bundle of threads or multi-filaments or fibers or fibrils made from biocompatible and biodegradable materials, and the like. In one embodiment the composition can be placed at the interface between a skin graft or skin flap and underlying tissue of a mammalian subject. In other embodiment at least one composition is attached to the skin graft or skin flap. In some other embodiments a laser ablation is used to introduce the composition into the skin graft or skin flap. The composition provides a targeted delivery of growth factors such as Vascular Endothelial Growth Factors or Hepatocyte Growth Factors or suitable cells including iPS cells, bone marrow, adipose, or other stem cells, platelet rich plasma, and the like. The controllable degradation of the bundle enables a suitable growth factor release profile. In a preferred embodiment, the healing agent is present in the composition in an amount effective to reduce edema or increase perfusion at the skin graft or skin flap, thereby improving the healing of the skin graft or skin flap.

In another embodiment, the mammalian subject is a human. In another preferred embodiment, the mammalian subject is a horse.

In one embodiment, the methods of the present invention further include a step of attaching the transferred or transplanted tissues, such as the skin graft of skin flap, to the underlying tissue. In one variation, the administering of the composition precedes the attachment. Alternatively, the administering of the composition occurs subsequent to the attaching. In a preferred variation, the attaching step includes surgical connection of blood vessels between the underlying tissue and the skin graft or skin flap.

In still another embodiment of the present invention provides a method of improving the healing of a skin graft or skin flap to underlying tissue of a mammalian subject wherein the skin graft or skin flap is attached in an abdominoplasty (abdominal lipectomy) or liposuction procedure.

The materials and methods of the present invention may be practiced with a skin graft that is a split thickness, full thickness, or composite graft, and/or a skin flap that is a local flap, a regional flap, a musculocutaneous flap, an osteomyocutaneous flap and/or a soft tissue flap. One can also contemplate the use of in vitro epidermal keratinocyte cultures and epidermal sheets formed therefrom into which the composition has been transfected. The epidermal sheets are administered to a patient, for example, to promote reepthelialization of burn wounds.

In a further embodiment, the present invention provides a method of inhibiting tumor metastases comprising: performing reconstructive surgery following excision of a tumor from a mammalian subject, said surgery including transferring or transplanting a lymph node or lymph node fragment; and administering a composition to promote survival of the lymph node and integration of the lymph node into a lymphatic network in the mammalian subject, at the site of transfer or transplantation.

As an alternative to being included in a composition of the present invention including a first protein, a second protein or a therapeutic agent may be concurrently administered with the first protein (e.g., at the same time, or at differing times provided that therapeutic concentrations of the combination of agents is achieved at the treatment site).

The composition(s) used to practice methods of the present invention optionally comprise additional materials besides the healing agent. For example, the composition preferably includes a pharmaceutically acceptable carrier.

In still another variation, endothelial cells, endothelial progenitor cells, smooth muscle cells, or keratinocytes are transfected ex vivo with the composition, and the transfected cells are administered to the mammalian subject. Also keratinocytes can be transfected in vitro and then administered to the subject.

In one embodiment, the heparin or multi arm PEG are used to attach the growth factors to the bundle of threads or multi-filaments or fibers or fibrils made from biocompatible and biodegradable material.

The compositions are also presently valuable for veterinary applications. It based on lymphedema pig animal study. Particularly domestic animals and thoroughbred horses, in addition to humans, are desired patients for such treatment with a composition of the present invention.

Likewise, the present invention also provides surgical devices that are used to reduce edema or increase perfusion at the free flap, skin graft or skin flap comprising the composition.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations specifically mentioned above. With respect to aspects of the invention described as a genus, all individual species are individually considered separate aspects of the invention. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention. Additional features and variations of the invention will be apparent to those skilled in the art from the entirety of this application, and all such features are intended as aspects of the invention.

BRIEF DESCRIPTION OF THE DRAWINGS

The accompanying drawings, which are incorporated in and constitute a part of this specification, exemplify embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not necessarily drawn to scale.

FIG. 1B is the SEM image of its cross section; FIG. 1C is the microscopic image of human microvascular endothelial cells (hMECs) attached and aligned along the device; FIG. 1D is the AFM image of aligned collagen-based fibrils/fibers of aligned-braided or simple crimp fibril/fiber structure that composes the device; FIG. 1E is the SEM image of the cells aligned along the device.

FIG. 2A is the AFM image of aligned collagen-based fibrils/fibers of aligned-crimp structure that composes the BioBridge device; FIG. 2B is the image of the ribbon that forms the device; FIG. 2C is the image of the thread-like device; FIG. 2D are the SEM images of the device cross sections.

FIG. 3A-3B are the SEM images of BioBridge device with attached endothelial cells; FIG. 3C is the cell staining for CD31 (green) and nuclei (blue); FIG. 3D is the cell staining for Ki67 (red) and nuclei (blue). Arrow denotes direction of 30 nm collagen-based fibrils/fibers.

FIG. 4A is the VEGF-C-conjugated BioBridge samples were incubated in collagenase I or PBS for 6 days with medium collected and replaced at each time point. VEGF-C content in the collected samples was plotted as percentage on total amount released in experiment (n≥3). FIG. 4B is the comparison of total VEGF-C release values from BioBridge samples at different VEGF-C concentrations used at the incubation step; data are shown as normalized to a 1-cm sample and to µg heparin covalently bound on sample (n≥3).

FIG. 16A—the use of BioBridge in Vascularized Lymph Node Transfer (VLNT) procedure (e.g. Dr. Becker procedure); FIG. 16B—the preventive treatment (e.g., after lymph node resection and/or irradiation); FIG. 16C—the treatment by the Composition implantation (e.g. lymph node fragments and thread-like device).

DETAILED DESCRIPTION

Figure 1:
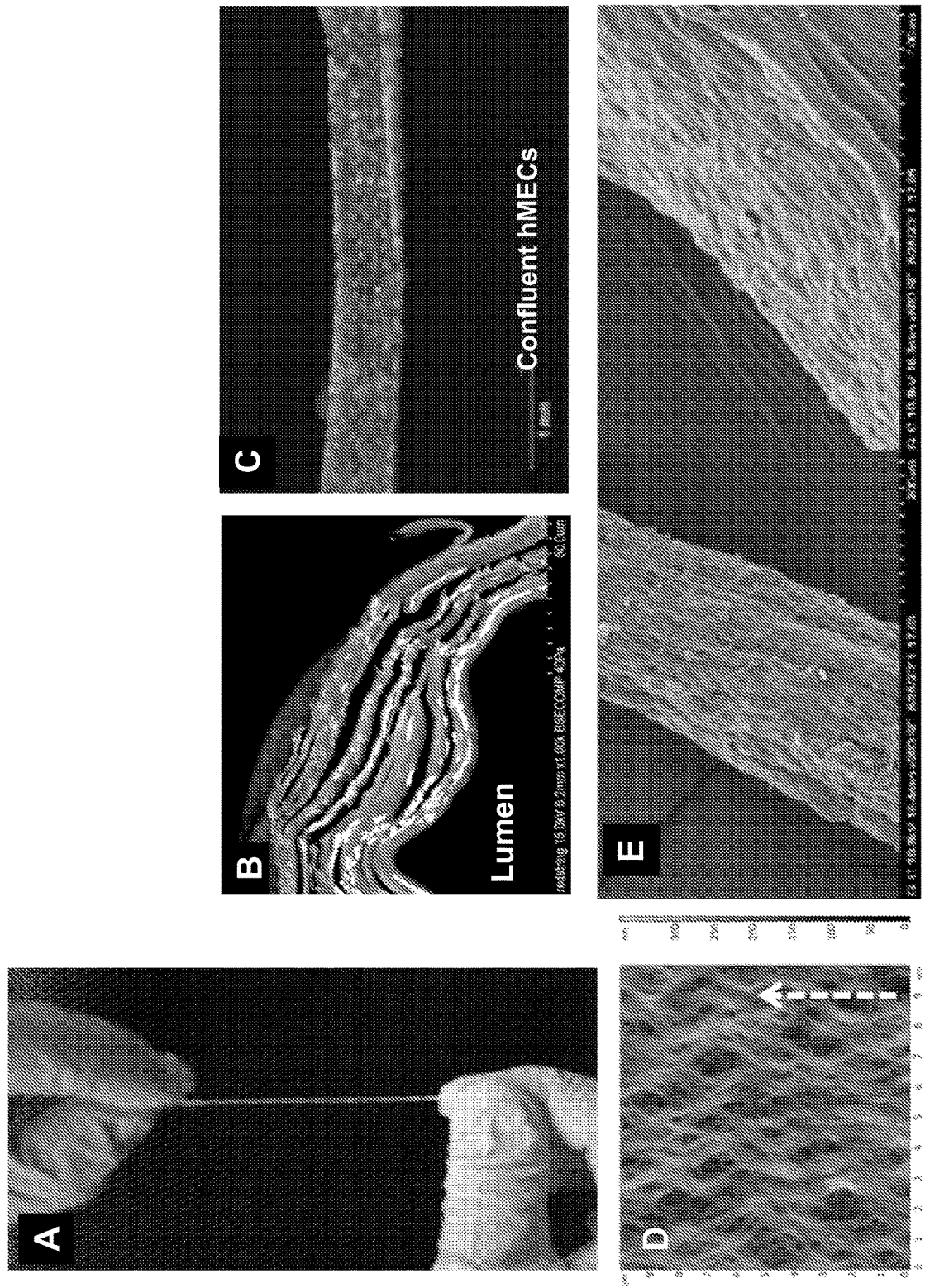
FIGS. 1A-1E: The thread-like collagen-based multi-lumenal device (hereinafter referred to as "BioBridge") according to embodiments of the present invention is presented in FIG. 1A.
Figure 2:
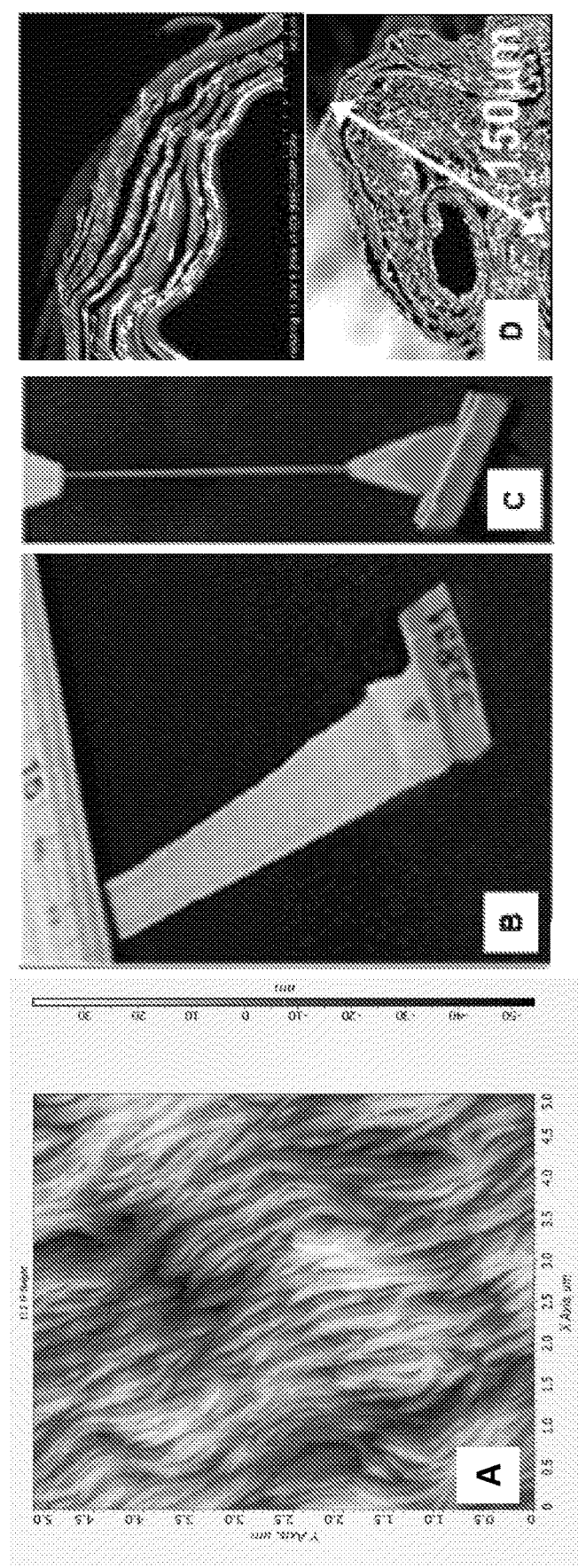
FIGS. 2A-2D.

The present invention provides materials and methods to improve healing of skin and/or underlying tissue (tissue with or without a lymph node or lymph node fragment) or adjacent tissues or limbs following a surgical procedure.

Reconstructive surgery is generally performed on abnormal structures of the body, caused by birth defects, developmental abnormalities, trauma or injury, infection, tumors, or disease. It is generally performed to improve function, but may also be done to approximate a normal appearance. Cosmetic surgery is performed to reshape normal structures of the body to improve the patient's appearance and self-esteem.

Complications resulting from reconstructive and cosmetic surgery may include infection; excessive bleeding, such as hematomas (pooling of blood beneath the skin); significant bruising and wound-healing difficulties; pain; edema; and problems related to anesthesia and surgery. The methods and compositions described herein provide a much-needed treatment to improve post-surgical wound healing.

Many common reconstructive and cosmetic surgery procedures result in painful swelling and bleeding where skin flaps and/or grafts are used. In breast augmentation, breast reduction, mastopexy and gynecomastia procedures, for example, fluid accumulation and swelling may result, possibly requiring subsequent corrective surgical procedures. In such procedures, skin of and around the nipple is separated and/or removed from the underlying breast tissue. A skin flap or skin graft is frequently necessary to compensate for the change in breast size and/or to gain access to underlying tissues for implantation or reduction. Accordingly, the methods and compositions of the present invention can be used to promote wound healing prior to, during, and/or following the aforementioned surgical procedures.

Similarly, cosmetic surgery procedures such as rhytidectomy, browlift, otoplasty, blepharoplasty, rhinoplasty, facial implant, and hair replacement therapy will also benefit from the present invention. In such procedures, skin is lifted and underlying tissue and muscles are removed or manipulated. A skin flap or skin graft is frequently necessary to compensate for skin tissue loss and/or to gain access to the tissues and muscles beneath the skin. Accordingly, the methods and compositions of the present invention can be used to promote wound healing prior to, during, and/or following the aforementioned surgical procedures.

In an abdominoplasty procedure, the abdomen is flattened by removing excess fat and skin and tightening muscles of the abdominal wall. Bleeding under the skin flap and poor healing resulting in skin loss and scarring may occur, possibly requiring a second operation. Accordingly, the methods and compositions of the present invention can be used to promote wound healing prior to, during, and/or following the aforementioned surgical procedure.

Reconstructive surgery procedures such as those to repair a birthmark, cleft palate, cleft lip, syndactyly, urogenital and anorectal malformations, craniofacial birth defects, ear and nasal deformitites or vaginal agenesis similarly involve incisions and manipulations in skin and underlying tissues for the restoration of body features. A skin flap or skin graft is frequently necessary to compensate for skin tissue loss and/or to gain access to the tissues and muscles beneath the skin. Accordingly, the methods and compositions of the present invention can be used to promote wound healing prior to, during, and/or following the aforementioned surgical procedures.

Similarly, reconstructive surgery to correct defects resulting from an injury such as a burn, infection, or disease such as skin cancer will also benefit from the compositions and methods of the present invention. For example, an oseomyocutaneous flap (a flap containing bone and soft tissue) is often used to reconstruct the skin following skin cancer excision. Thus, the present invention may be employed to reduce the swelling and scarring complications associated with such a procedure.

In general, a flap is a section of living tissue that carries its own blood supply and is moved from one area of the body to another. Flap surgery can restore form and function to areas of the body that have lost skin, fat, muscle movement, and/or skeletal support.

A local flap uses a piece of skin and underlying tissue that lie adjacent to the wound. The flap remains attached at one end so that it continues to be nourished by its original blood supply, and is repositioned over the wounded area. A regional flap uses a section of tissue that is attached by a specific blood vessel. When the flap is lifted, it needs only a very narrow attachment to the original site to receive its nourishing blood supply from the tethered artery and vein. A musculocutaneous flap, also called a muscle and skin flap, is used when the area to be covered needs more bulk and a more robust blood supply. Musculocutaneous flaps are often used in breast reconstruction to rebuild a breast after mastectomy. This type of flap remains "tethered" to its original blood supply. In a bone/soft tissue flap, bone, along with the overlying skin, is transferred to the wounded area, carrying its own blood supply.

Typically, a wound that is wide and difficult or impossible to close directly may be treated with a skin graft. A skin graft is basically a patch of healthy skin that is taken from one area of the body, called the "donor site", and used to cover another area where skin is missing or damaged. There are three basic types of skin grafts.

A split-thickness skin graft, commonly used to treat burn wounds, uses only the layers of skin closest to the surface. A full-thickness skin graft might be used to treat a burn wound that is deep and large, or to cover jointed areas where maximum skin elasticity and movement are needed. As its name implies, a full-thickness (all layers) section of skin from the donor site are lifted. A composite graft is used when the wound to be covered needs more underlying support, as with skin cancer on the nose. A composite graft requires lifting all the layers of skin, fat, and sometimes the underlying cartilage from the donor site.

Microvascular free flap transfer generally entails the division and subsequent reanastomosis of the dominant artery and vein in a tissue, allowing the transplanted tissue to survive. A microvascular bed or free flap is an intact microcirculatory network or bed. Microvascular free flap transfer is the auto-transplantation of composite tissues (known as a free flap) from one anatomic region to another. As such, microvascular free tissue transfer represents the manipulation and transfer of an intact microcirculatory network or bed. This network can supply a variety of tissues because of its functioning micro-circulatory network. This vascular network may be detached from the intact organism and maintained ex vivo, permitting its manipulation or modification without danger of systemic toxicity.

When the expendable microvascular beds are in their normal, native state, they contain all of the distinct, constituent cells that exist within the microcirculation. Grossly, they consist of large muscular arteries, leading to capacitance arterioles, endothelial lined capillaries, venules, veins and all of the phenotypically distinct cells within them. Importantly, in the native state, they contain all of these cell types in a functional and precisely ordered three-dimensional configuration. In a sense, they have already been "patterned." These expendable microvascular beds provide an ideal, living substrate on which to fabricate a "neoorgan," i.e., a non-naturally occurring vascularized tissue that provides a function of a gland or organ, or that supplements the function of a gland or organ. Since microvascular free flaps contain a single afferent artery and efferent vein they can be reintegrated into the systemic circulation by standard vascular anastamoses.

According to the methods of the present invention, a tissue of interest (i.e., microvascular free flap) is harvested as an explant for modification and subsequent reattachment or reanastomosis, e.g., to reconstruct defects following tumor extirpation such as in a mastectomy. In performing microvascular free flap transfer, an intact microcirculatory network or bed is detached. According to one exemplary method of the invention, this vascular network is detached from the intact organism for a finite period of time (ex vivo), and undergoes modification, e.g., by protein therapy or genetic modification, and in a certain embodiments, by transfection with a polynucleotide encoding a therapeutic polypeptide.

According to an exemplary method of the invention, a selected tissue may be excised ("harvested") by conventional surgical methods known in the art. The surgical procedure results in the removal of skin and subcutaneous tissue associated with blood vessels in a select region of the body.

In another aspect of the invention, a composite tissue flap, i.e., a flap composed of bone and skin, muscle and skin, adipose tissue and skin, fascia and muscle, or other such combination known to normally be present in the vertebrate body, is used because it has a greater tolerance for ischemia, allowing for more extensive manipulation prior to reanastomosis, including an attachment to a composition of the invention.

Once the flap is excised, the proximal blood vessels that are associated with the flap are clamped. Any technique known in the art can be used to clamp the blood vessels.

The selected tissue is maintained ex vivo by methods for maintaining explants well-known in the art. The tissue is preferably perfused, e.g., the tissue can be wrapped in gauze, a catheter can be placed in a blood vessel associated with the tissue and secured with a suture, and the tissue perfused or infused with physiological saline. In one embodiment, the perfusion is conducted at a cold temperature (for cold ischemia). In other embodiments, perfusion is conducted at room temperature or body temperature. Preferably, the tissue is perfused ex vivo through a catheter at a constant perfusion pressure to flush out blood from the flap vessels. Preferably, the infusions are given at physiologic pressures (80-200 mm Hg), since high pressures cause excessive tissue damage, leading to necrosis of all or part of the flap. In one embodiment, a continuous microperfusion system is used.

In other embodiments, an explanted flap can be maintained for a prolonged period of time by using an immunodeficient host as a recipient.

Using conventional surgical procedures, the flap is then reinserted into the patient and re-anastomosed to a section of the circulatory system in the patient. Preferably, the flap is attached non-orthotopically, i.e., it is reanastomosed to a different area of the patient's circulatory system. For example, a flap may be detached from its supply from the femoral artery, transfected by perfusion, then transplanted to the region of the carotid artery and attached to the carotid arterial system. In another embodiment, the flap is reattached to the blood vessels from which it was excised. Preferably, a splint or other protective device is placed over the operative site after attachment or reanastomosis.

In certain cases, reimplantation of the microvascular free flap may produce a substantial degree of scarring, thus obscuring the viability of the tissue independent from surrounding tissue. If this occurs, methods commonly known in the art, such as separation with silicone sheets, may be utilized to separate a reimplanted microvascular free flap from the host in order to inhibit tissue ingrowth.

The microvascular free flaps or beds can also comprise tissue derived from organs or organ systems such as the skeletal system (including bones, cartilage, tendons and ligaments); the muscular system (including smooth and skeletal muscles); the circulatory system (including heart, blood vessels, endothelial cells); the nervous system (including brain, spinal cord and peripheral nerves); the respiratory system (including nose, trachea and lungs); the digestive system (including mouth, esophagus, stomach, small and large intestines); the excretory system (including kidneys, ureters, bladder and urethra); the endocrine system (including hypothalamus, pituitary, thyroid, pancreas and adrenal glands); the reproductive system (including ovaries, oviducts, uterus, vagina, mammary glands, testes, seminal vesicles and penis); the lymphatic and immune systems (including lymph, lymph nodes and vessels, white blood cells, bone marrow, T- and B-cells, macrophage/monocytes, adipoctyes, keratinocytes, pericytes, and reticular cells.

The techniques employed for an Autologous lymph node transplantation are generally those as previously described by Becker et al., Ann. Surg., 243:313-315, 2006, incorporated by reference herein, with the addition of the composition described in this invention. Briefly, surgical approach of the axillary region of the lymphedematous limb is performed in search of receiving vessels: fibrotic muscular and burned tissue are dissected and adhesions released. Axillary vessels are dissected and the periscapular pedicle is isolated. The circumflex posterior branches are individualized and prepared for microanasto-moses.

Next, an incision is performed in the inguinal region. These nodes are dissected, freed, and elevated external to internal at the level of the muscular aponeurosis. The nodes are then harvested with an abundant amount of surrounding fat tissue. Lymph nodes are then transplanted in the axillary receiving site. Artery and vein are anastomosed with the vessels previously prepared, using microsurgical techniques. Alternatively, a "double flap" is utilized. A double flap is harvested from the abdominal wall containing lymph nodes and fat and skin for breast reconstruction.

Exemplary human patient populations that would benefit from the methods of the present invention include patients with vascular reconstruction and postoperative lymphedema, trauma patients with secondary lymphedema, patients with primary lymphedema, caused by local lymph node hypoplasia, and patients with vulva/uterus/ovarian/testicular carcinoma and post-operative lymphedema.

There are a number of patient factors that severely limit the likelihood of successful microvascular free tissue transfer. Age in and of itself may not be important; however, many serious systemic diseases are more often found in patients of advanced age. Severe cardiovascular disease and atherosclerosis may compromise flap vessels. Diabetes impairs wound healing and negatively affects vessel health. Connective tissue disorders may also compromise the cardio-vascular system. Prior irradiation, diabetes (well-controlled), method of anastomosis, timing, vein graft, and specific arteries/veins are not felt to contribute to flap failure rate. The effect of nicotine on flap failure is controversial.

Proper care after the surgery requires personnel who understand the basic principles of free flap reconstruction. Pressure in the vicinity of the pedicle (including tracheotomy ties or dressings) is avoided. Supplemental oxygen, or humidified air can cool a superficial flap and inhibit its blood flow.

8-20% of patients undergoing free tissue transfer will develop an infection. The effects of post-operative infection can be serious in the area of a free flap anastomosis. Therefore the addition of silver nanowires into the composition could be beneficial.

The following patents and patent applications are fully incorporated by reference herein in their entirety: U.S. Pat. No. 8,513,382, International Patent Application Publication No. WO/2013/103423, U.S. Patent Publication No. 2012/0065703, International Patent Application Publication No. WO/2012/034110, and International Patent Application Serial No. PCT/US2013/051906.

Of particular advantage, embodiments of the present invention provide a novel composition. In one embodiment, the composition is an implant that may comprise a bundle of threads or multi-filaments or fibers or fibrils made from biocompatible and biodegradable materials, which induce capillary flow of extracellular fluid in the bundle direction, promote endothelial cell survival and cell migration along the bundle, and preserve endothelial cell phenotype. The composition is intended to be implanted to a site of disrupted lymphatic network or to a gap between the healthy lymphatics or to connect the transferred lymph node or lymph node fragments to healthy lymphatics. The composition may include lymph nodes or lymph node fragments. The examples of lymph nodes or lymph node fragments are the autologous lymph nodes or allogeneic lymph nodes or decellularized lymph nodes or lymph node fragments. The composition may also include the attached or encapsulated growth factors or drugs or diagnostic markers (e.g., iron oxide nanoparticles or other MRI or CT markers), or neuroelectrical stimulators using external magnetic field, or micro-pump (e.g., piezoelectric micro-pump using external magnetic field) to pump extracellular fluid. The bundle of fibers or fibrils presented in the composition is effective to stimulate and direct the formation of new lymphatic and blood vessels. The bundle of fibers or fibrils presented in the composition is effective to promote survival of the lymph node or lymph node fragments and integration of the lymph node or lymph node fragments into a lymphatic network in the mammalian subject, at the site of transfer or transplantation.

Of significant advantage, in some embodiments the composition of the present invention is used in a surgical method for reconstruction and/or repair of the alymphatic area. Lack of sufficient or healthy lymphatic vessels or lymph nodes in some area of the human or animal body may cause a chronic accumulation of lymph fluid in the tissues and organs called lymphedema. Such area is called herein an "alymphatic area". In particular, we refer to the impacted area that is causing a barrier to the effective drainage of interstitial fluid as the "alymphatic area". For example, it can be the area of a scar.

In some embodiments, the composition is composition is provided as, or formed in, a thread-like device. Three dimensional biocompatible scaffold or graft which has one dimension much higher than two other dimensions. The examples are the thread-like collagen scaffold (or thread); or a fibrin thread; or suture; or thread-like ECM; or thread-like decellularized tissue; or a thread supporting, reconnecting, and repairing soft tissue including lymphatic tissue; or microfibrillar thread; or a thread with micro-foam inclusion. We also refer to this device here as BioBridge, and as shown in detail illustratively in FIGS. 1A-1E. The thread-like device is a special type of the composition.

In one embodiment, a thread-like device may be used as is further described and illustrated in U.S. Pat. No. 8,513,382, the entire disclosure of which is hereby incorporated by reference.

In other embodiments the thread-like device is shown in FIGS. 1A-1E and FIGS. 2A-2D. FIG. 1A and FIG. 1B is a SEM image of its cross section. FIG. 1C is a microscopic image of human micro-vascular endothelial cells (hMECs) attached and aligned along the device. FIG. 1D is an AFM image of aligned collagen-based fibrils/fibers of aligned-braided or simple crimp fibril/fiber structure that composes the device. FIG. 1E is a SEM image of the cells aligned along the device.

FIG. 2A also shows an AFM image of aligned collagen-based fibrils/fibers of aligned-crimp structure that composes the BioBridge device. FIG. 2B is an image of the ribbon that forms the device. FIG. 2C is an image of the thread-like device. FIG. 2D are SEM images of the device cross sections.

In some embodiments, an implantation device is used to deliver the composition into alymphatic area or a cell-guiding device to provide means for cell migration. In one example, the implantation device is a slider cassette. The slider cassette is broadly comprised of a support plate and a lid. The composition is placed on the support plate, and the lid is disposed on top of the composition to protect and cover the composition.

In some embodiments, the lid is made from medical grade plastic. The typical shape of the lid is a thin ribbon. One possible plastic type is PET with hydrophobic surface coating to ease the lid removal after implantation of the slider cassette with construct into the subcutaneous tunnel in alymphatic area.

There are two preferred embodiments for the design of the support plate. In the first embodiment, the support plate is made from medical grade steel such that it is a thin plate with rectangular shape having a grooved surface to carry the thread-like devices, e.g., thread-like collagen scaffold. It may have slots to insert the lid. In this case the support plate and lid should be removed after implantation leaving the construct in the subcutaneous tunnel of the alymphatic area. In a second embodiment, the support plate is implanted into subcutaneous tunnel together with the composition or without the composition. In the latter case it should promote the attachment and migration of cells from alymphatic area periphery and induce formation of lymphatic system bridging the alymphatic area.

Figure 8:
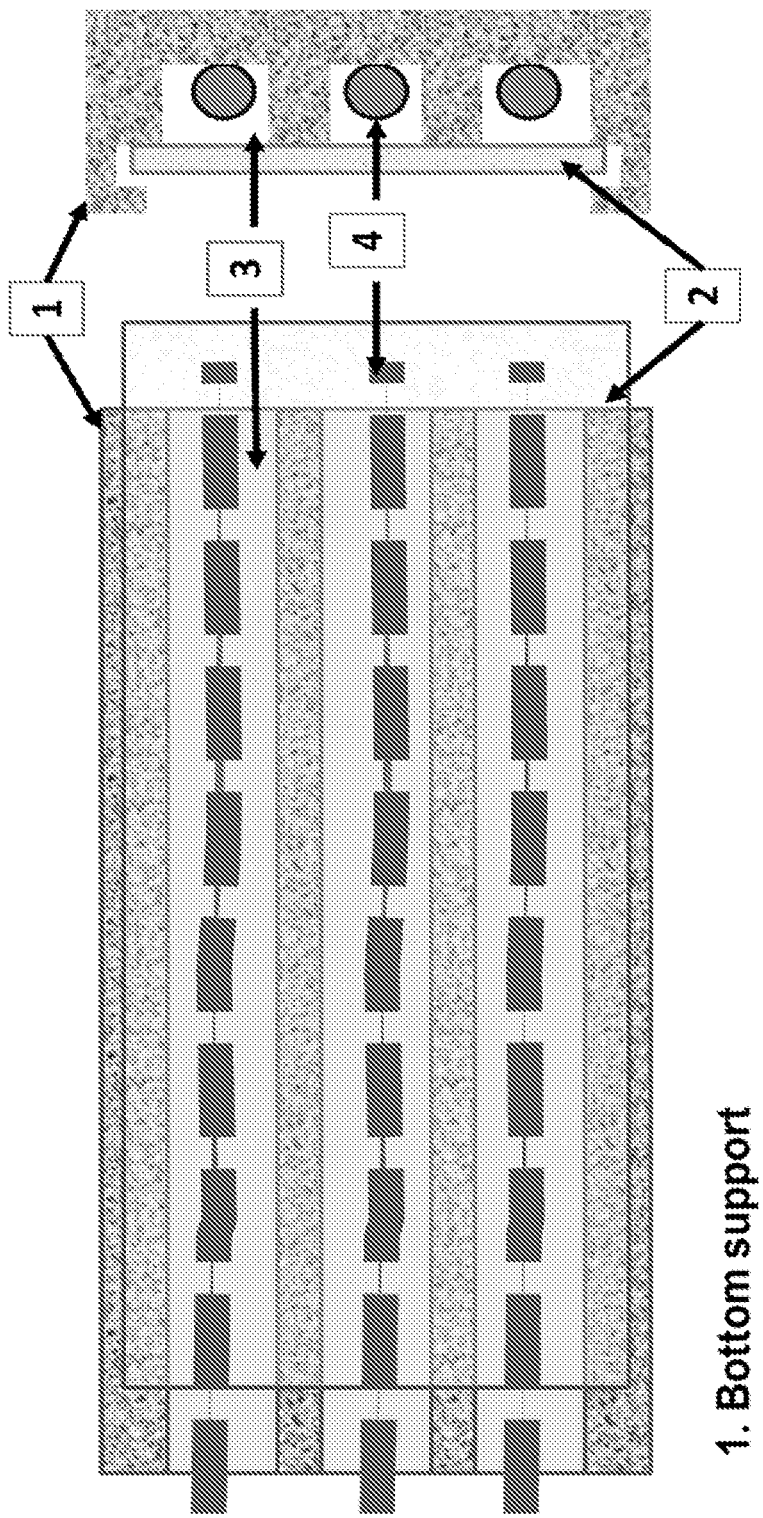
FIG. 8: Top view and cross view of the slider cassette used for the thread-like device implantation.

FIG. 8 illustrates one example of the slider cassette showing a top view and cross-section view of a slider cassette used for the thread-like device implantation. In the exemplary embodiment, slider cassette is comprised of bottom support 1 and top lid 2. The bottom support 2 includes one or more grooves 3 formed therein. Grooves 3 are formed in such a manner as to carry the threads 4 of the thread-like device.

Figure 6:
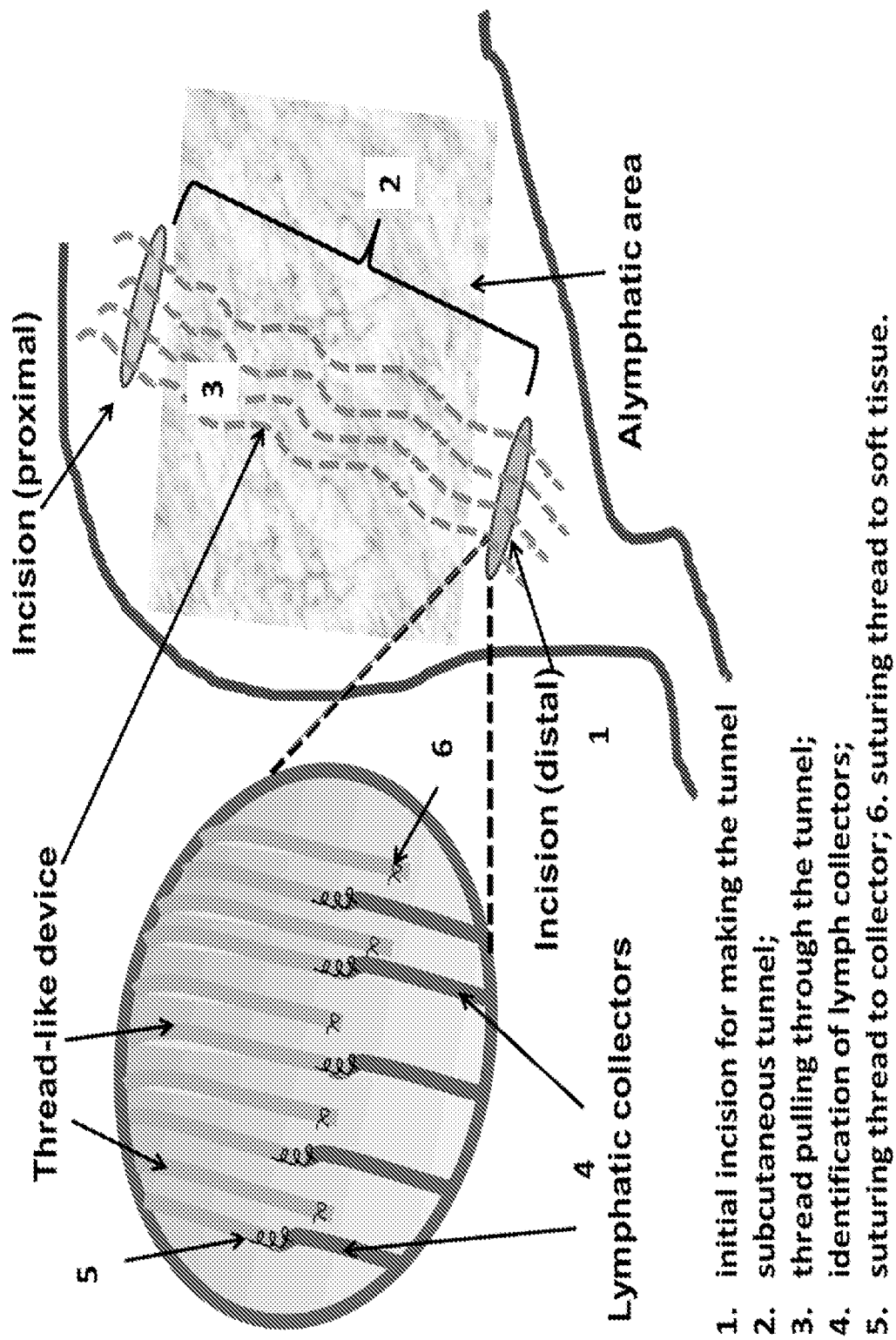
FIG. 6: Details of the composition (thread-like device) implantation: (1) initial incision for making the tunnel; (2) subcutaneous tunnel; (3) composition (thread) pulling through the tunnel; (4) identification of lymph collectors; (5) suturing thread to collector; (6) suturing thread to soft tissue.
Figure 9:
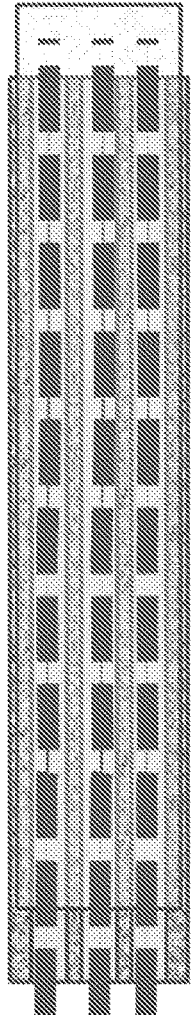
FIG. 9: Detail explanation of the procedure for the thread-like device implantation using the slider cassette.
Figure 9:
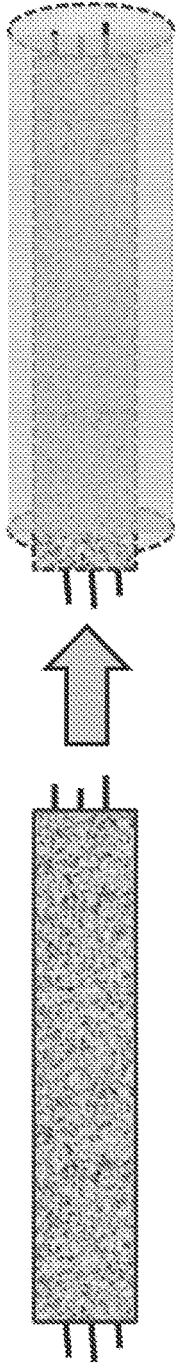
Figure 9:
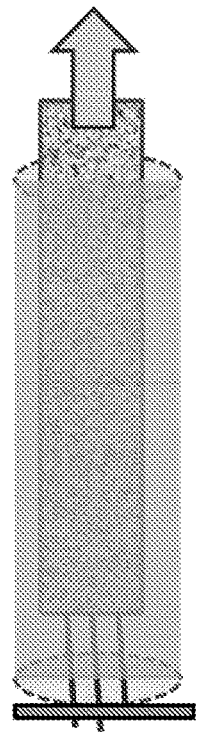
Figure 9:
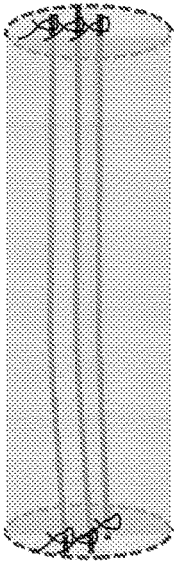

An example of one procedure for implanting the thread-like device using the slider cassette is shown in FIG. 9, with a general illustration shown in FIG. 6. Referring to FIG. 9, in a first step, the threads 4 are loaded into the grooves 3 in the bottom plate 1 and are then secured with the lid 2. In a second step, the slider cassette is inserted into the subcutaneous tunnel. In a third step, the threads 4 are held in place with a clamp and the slider cassette is pulled out of the subcutaneous tunnel. In a final step, the threads 4 are secured with sutures.

Figure 10:
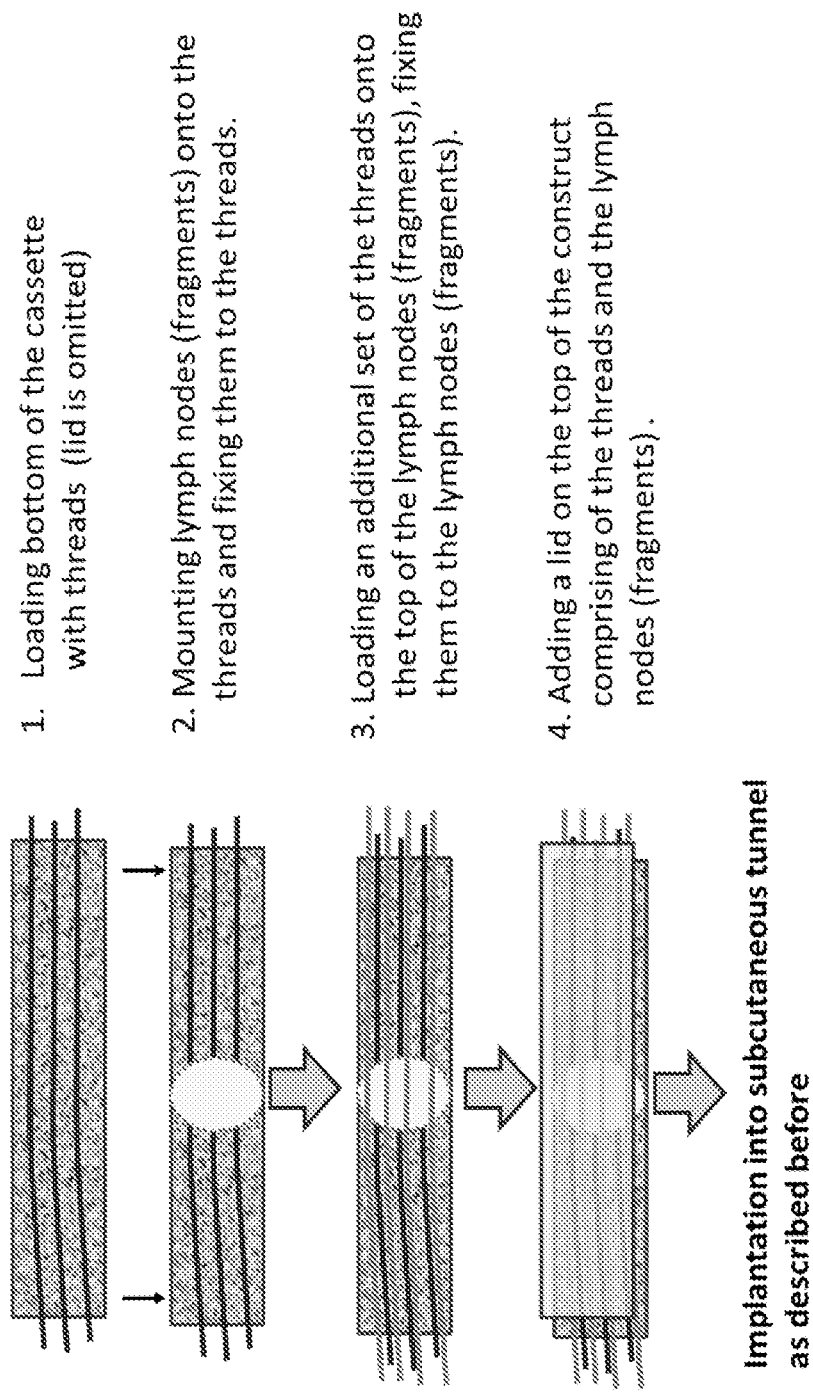
FIG. 10: Detail explanation of the procedure for the thread-like device and lymph node fragment implantation using the slider cassette.

FIG. 10 illustrates another embodiment. In this embodiment, a procedure for implanting the thread-like device with lymph node fragment implantation using the slider cassette is provided. In a first step, the treads 4 are loaded on the bottom of the cassette. The lid is omitted in this step. In a second step, lymph nodes (fragments) are then mounted onto the threads and fixed to the threads. Optionally, in a third step, another set of threads may be loaded onto the top of the lymph nodes (fragments) and then fixed to the lymph nodes (fragments). Then, the entire construct comprised the threads and lymph nodes (fragments) are secured with the lid. The slider cassette with construct is then implanted into the subcutaneous tunnel in the same manner as illustrated in FIG. 9.

Growth factors may be included in the composition. Any suitable growth factor may be used, such as VEGF and HGF, and in particular, VEGF-C. FIGS. 4A-4B demonstrate analysis of VEGF-C release from BioBridge by ELISA. FIG. 4A is the VEGF-C-conjugated BioBridge samples were incubated in collagenase I or PBS for 6 days with medium collected and replaced at each time point. VEGF-C content in the collected samples was plotted as percentage on total amount released in experiment (n≥3). FIG. 4B is the comparison of total VEGF-C release values from BioBridge samples at different VEGF-C concentrations used at the incubation step; data are shown as normalized to a 1-cm sample and to μg heparin covalently bound on sample (n≥3).

Figure 5:
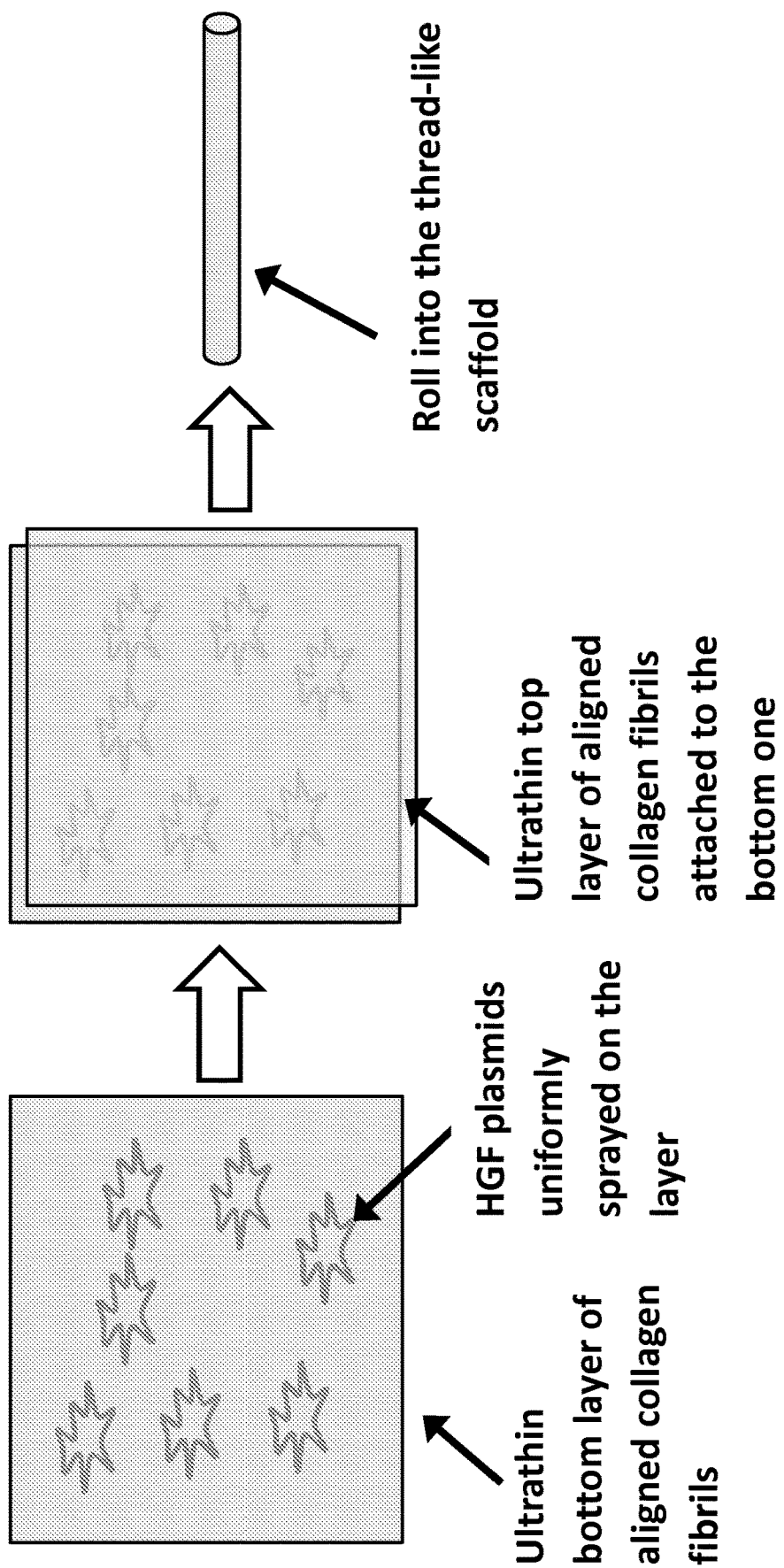
FIG. 5: The steps of the preparation of BioBridege with encapsulated Hepatocyte Growth Factor (HGF) plasmids. Ultra-thin (1-2 μm) collagen-based ribbons (membranes) are rolled into a thread-like scaffold with encapsulated HGF plasmids. Similar method is used to encapsulate homing factors into BioBridge.

Steps illustrating preparation of the composition (in this embodiment the BioBridge) with encapsulated Hepatocyte Growth Factor (HGF) plasmids is shown in FIG. 5. Ultra-thin (1-2 μm) collagen-based ribbons (membranes) are rolled into a thread-like scaffold with encapsulated HGF plasmids. Similar method is used to encapsulate homing factors into BioBridge.

Cells, such as bone marrow stem cells, iPS cells, endothelial cells, and the like, may also be employed. FIGS. 3A-3D show images of cells used with the thread-like device. For example, FIG. 3A-3B are SEM images of BioBridge device with attached endothelial cells. FIG. 3C is the cell staining for CD31 (green) and nuclei (blue). FIG. 3D is the cell staining for Ki67 (red) and nuclei (blue). Arrow denotes direction of 30 nm collagen-based fibrils/fibers.

Peptides may be included in the composition, such as without limitation, antibacterial peptides, the peptides which induce iPS cell differentiation, and the like Drugs and other suitable chemicals may be included, such as for example without limitation, anti-scarring drugs, antibacterial drugs, and the like.

In some embodiments, a laser may be beneficially used. For example, a Nd:YAG laser may be used or other suitable laser which is effective to remove scar tissue and make the subcutaneous tunnel or $CO_2$ laser or other which is in addition induce regeneration due to the thermal damage.

Figure 7:
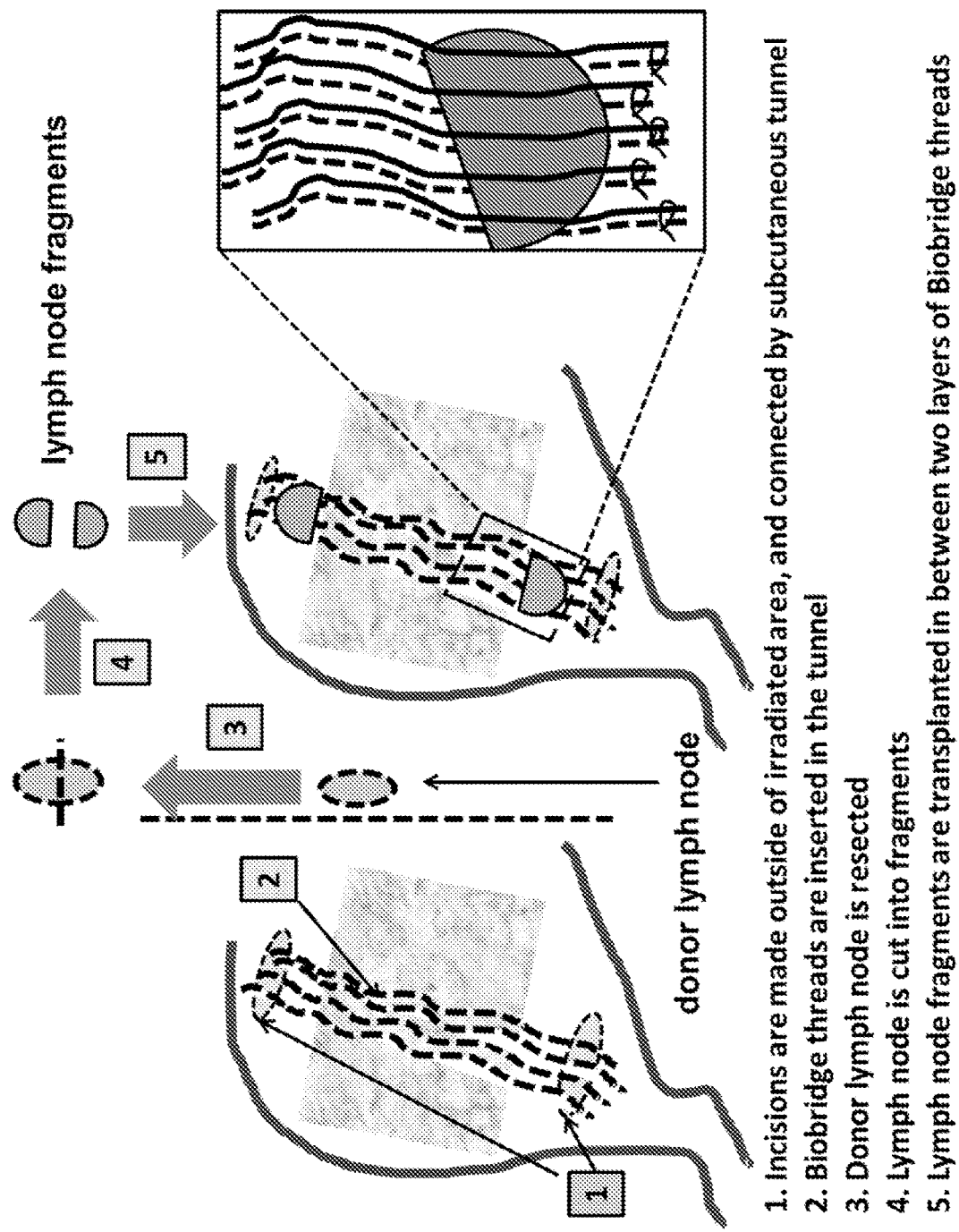
FIG. 7: Schematics of autologous lymph node fragment transplantation with thread-like device (threads). (1) Healthy donor lymph node excision; (2) cutting lymph node into fragments; (3) placement of the lymph node fragment between two layers of threads; (4) lymph node fragment with threads sutured to the soft tissue, prior to wound closure. Thread-like devices (a bundle of threads with aligned collagen-based fibrils/fibers) and lymph node fragments together constitute the composition.

As described above, a construct of the thread-like device with lymph node fragments may be employed. FIG. 7 shows schematics of autologous lymph node fragment transplantation with thread-like device (threads), in: (1) Healthy donor lymph node excision; (2) cutting lymph node into fragments; (3) placement of the lymph node fragment between two layers of threads; (4) lymph node fragment with threads sutured to the soft tissue, prior to wound closure. Thread-like devices (a bundle of threads with aligned collagen-based fibrils/fibers) and lymph node fragments together constitute the composition.

EXAMPLES

The following Examples further illustrate the invention. The Examples provided below are intended for illustration purposes only and in no way limit the scope and/or teaching of the present invention.

Example 1

Thread-like constructs (threads) made from collagen fibrils aligned in one direction (FIG. 1 and FIG. 2) were implanted in the subcutaneous tissue to bridge an alymphatic area (FIG. 6) in the right groin of a minipig (minipig lymphedema model). This area had been prior surgically depleted of all lymph vessels and lymph nodes and irradiated to inhibit local regeneration. To test the validity of the constructs, two small incisions were made proximally and distally of the alymphatic area in the right groin (FIG. 6). Lymphatic collectors in the healthy surrounding tissues were identified and partially separated from the fatty tissue near the distal incision site. Next, a subcutaneous tunnel following the axis of the right limb was created to embed the threads over a length of 10-12 cm. The threads arranged in 5 pairs running in parallel were inserted into the channel with hemostatic forceps. At the distal site, 5 threads were anastomosed with prolene 10-0 to the lymphatic collectors. The other distal thread ends, as well as all proximal thread ends, were fixed to the surrounding tissue with prolene 6-0.

Example 2

Thread-like constructs (threads) enriched with VEGF-C (similar to have shown in FIG. 5) were anastomosed to the collectors, as described in the Example 1. At the proximal site, the threads were sutured in pairs to the soft tissue. Wound closure was performed with 4-0 PDS sutures and 4-0 Procryl sutures intradermally.

Example 3

In lymph node fragment transfer supplemented with thread implantation, two small incisions and the subcutaneous tunnel between them were made as described above, followed by the procedure depicted in FIG. 7. Five pairs of threads with and without VEGF-C were inserted into the tunnel and kept separated into two layers, top and bottom (FIG. 6 and FIG. 7). The threads in the bottom layer were sutured to the soft tissue on both sides. Then, a healthy superficial inguinal lymph node (left groin) was excised with minimal injury to surrounding tissue. Thereafter, a transversal cut of the node into two equal fragments was performed to multiply induced regeneration foci. Each of the two lymph node fragments was transplanted subcutaneously into the tunnel opening in between two layers of threads and fixed to the superficial abdominal muscle fascia with non-resorbable prolene 6-0 suture. Thereafter, the top-layer threads were sutured to the soft tissue on both sides. Wound closure was performed as described above.

Example 4

The invented materials and methods are tested on porcine lymphedema model. This model has been developed in Hannover Medical School (Hadamitzky C, Pabst R. *Cancer Res.*, 2008, 68:343-345; K. S. Blum, et al. *Breast Cancer Res.*, 2010, 120: 59-66; and T. Sommer, et al. *Anat. Rec.*, 2012, 295: 786-91). A simplified version of the model is used in (M Lahteenvuo, et al. *Circulation*, 2011, 123: 613-620). This model is widely accepted as an adequate for secondary lymphedema surgical treatment. It has physiological, anatomical, functional similarity to human; comparable size; similarity in lymphedema induction (lymph node excision and radiation).

Figure 4:
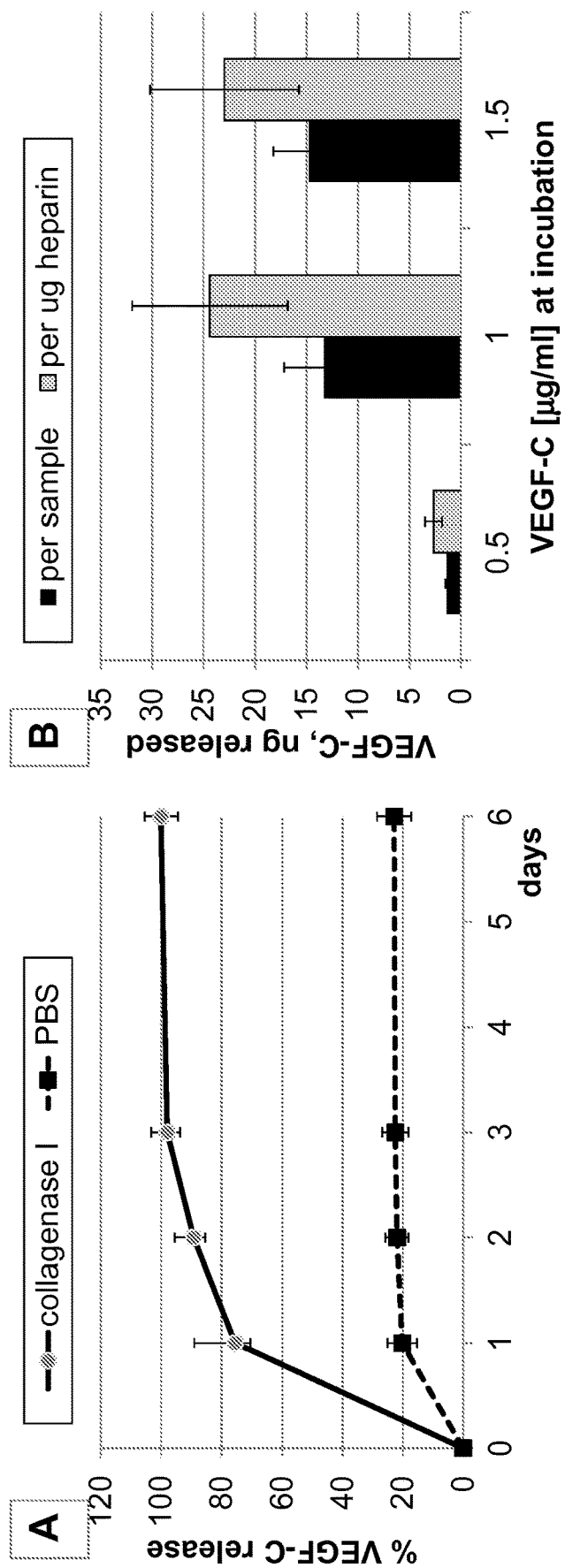
FIGS. 4A-4B: Analysis of VEGF-C release from BioBridge by ELISA.

Four types of composition have been tested in the porcine lymphedema model (see FIG. 11): a bundle of aligned collagen-based nano-fibers/fibrils in the form of a thread-like multiluminal scaffold; the thread-like multiluminal scaffold (FIG. 1 and FIG. 2) enriched by recombinant VEGF-C; fragments of autologous lymph node connected by the bundle of aligned collagen-based nano-fibers in the form of a thread-like multiluminal scaffold; fragments of autologous lymph node connected by the bundle of aligned collagen-based nano-fibers in the form of a thread-like multiluminal scaffold enriched by recombinant VEGF-C (the VEGF-C release profile is presented in FIG. 4).

Figure 3:
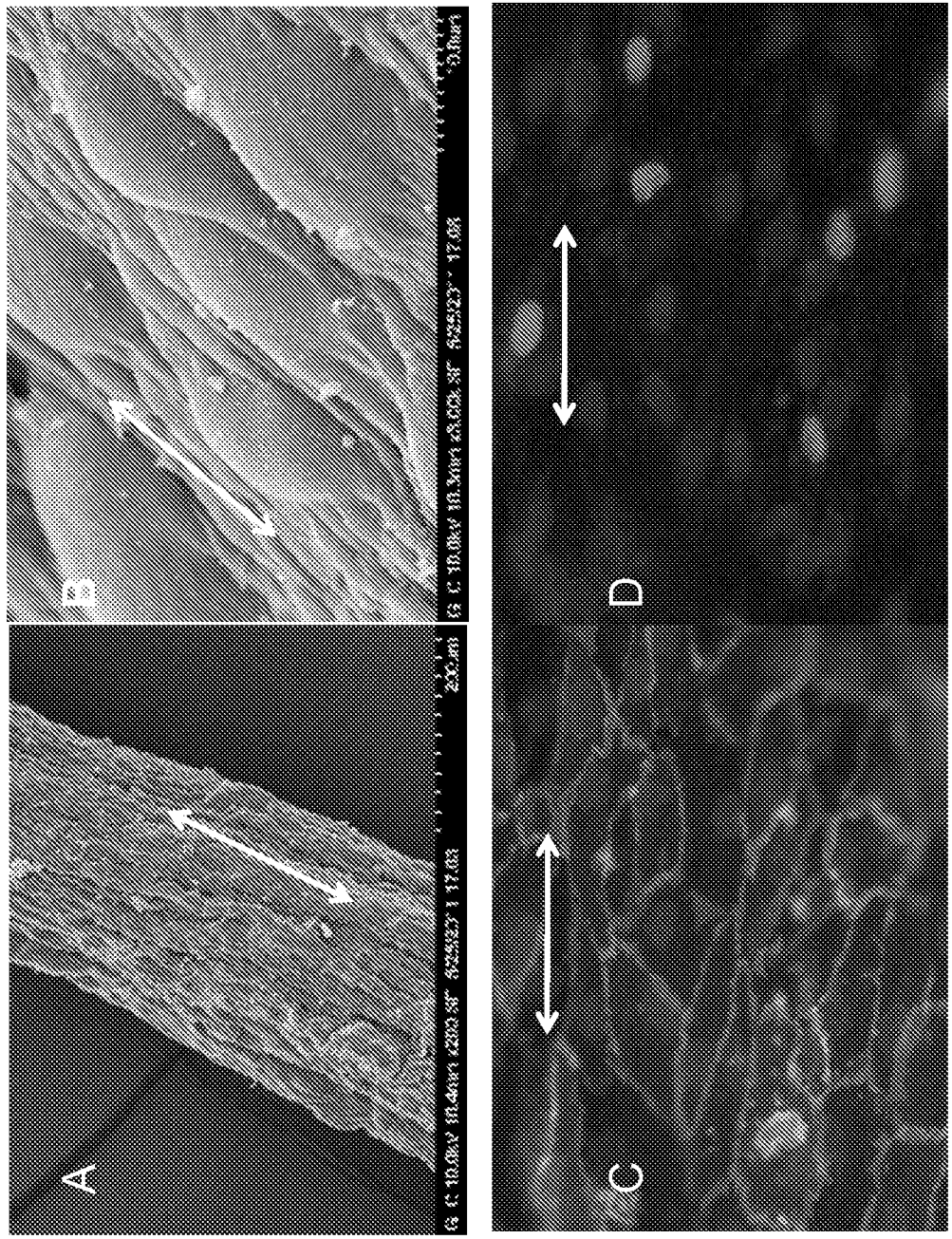
FIGS. 3A-3D.
Figure 11:
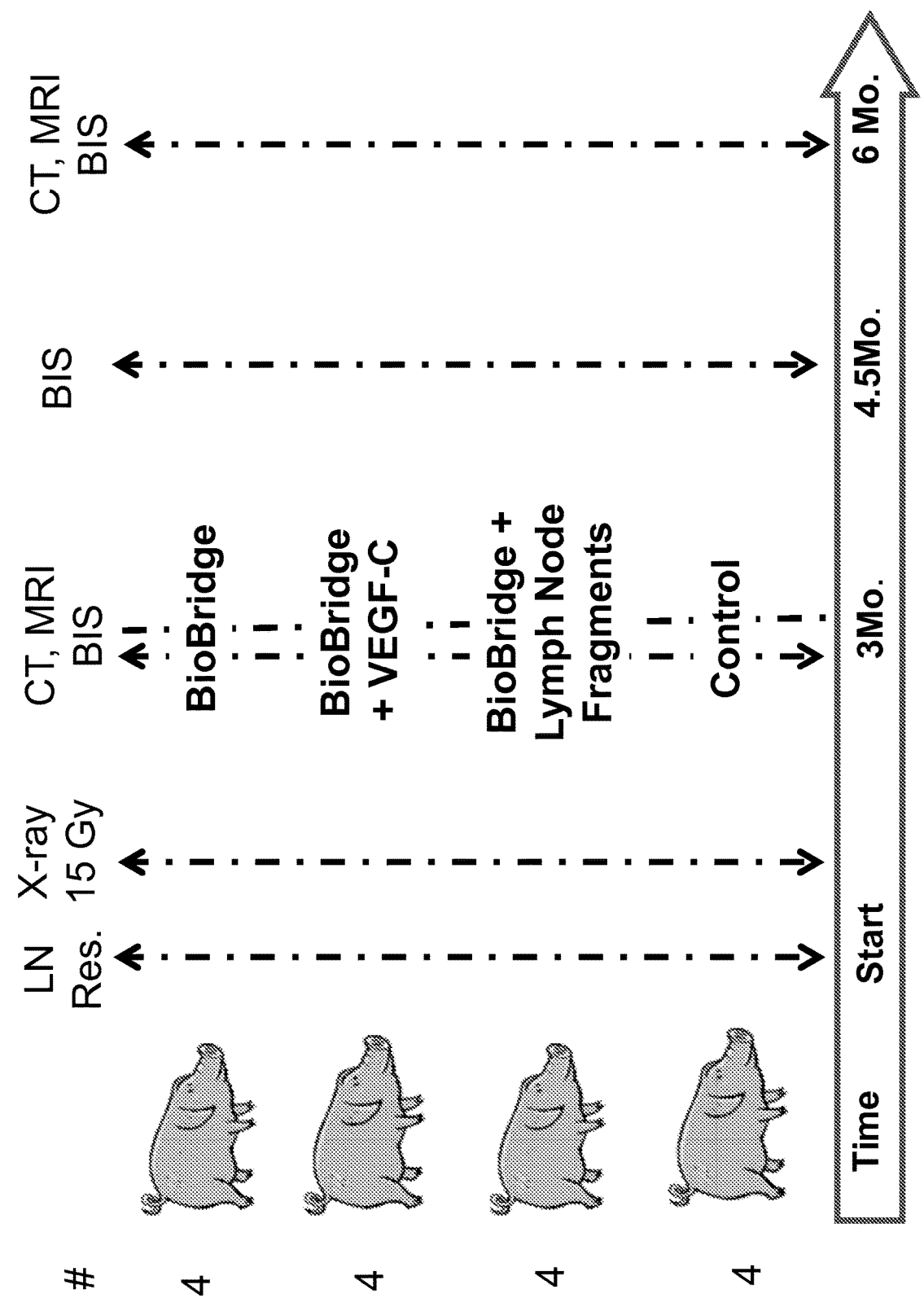
FIG. 11: Plan of porcine lymphedema animal model experiment described in the Example 4. BIS is the Bio-Impedance Spectroscopy measurements; MRI is Magnetic Resonance Imaging; CT—contrast enhance X-ray tomography measurements. LN Res. is the lymph node resection in the groin area of the right limb; X-ray is irradiation (15 Grey) of the groin area of the right limb after lymph node resection.
Figure 13:
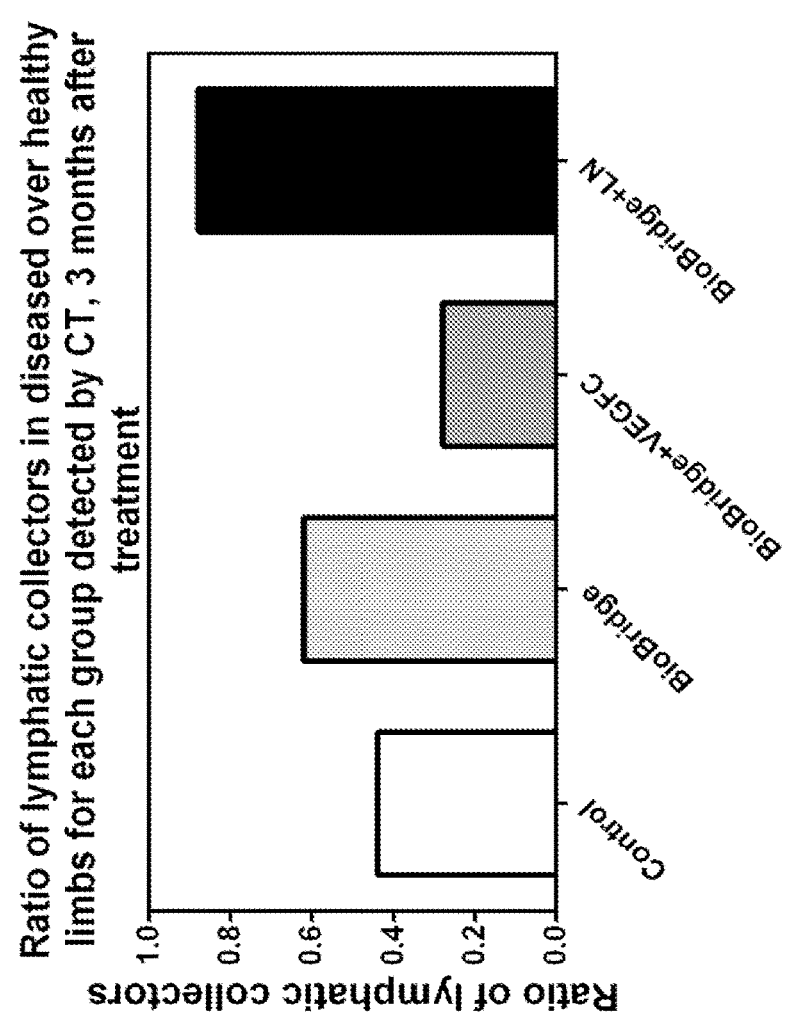
FIG. 13: Change in bioimpedance index (3 months after treatment) for each group is presented on the left and the ratio between average numbers of collectors detected by CT (3 months after treatment) for each group is presented on the right.
Figure 13:
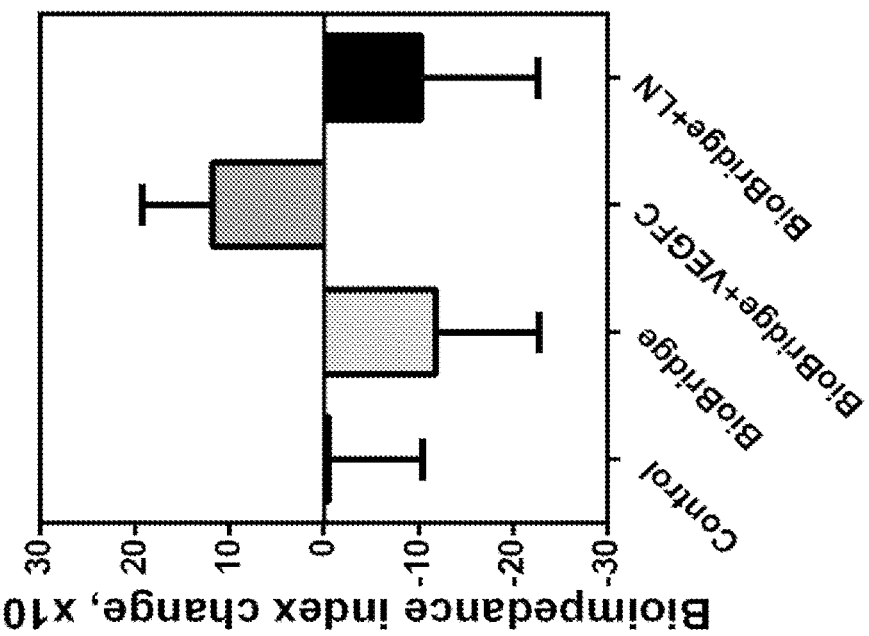
Figure 14:
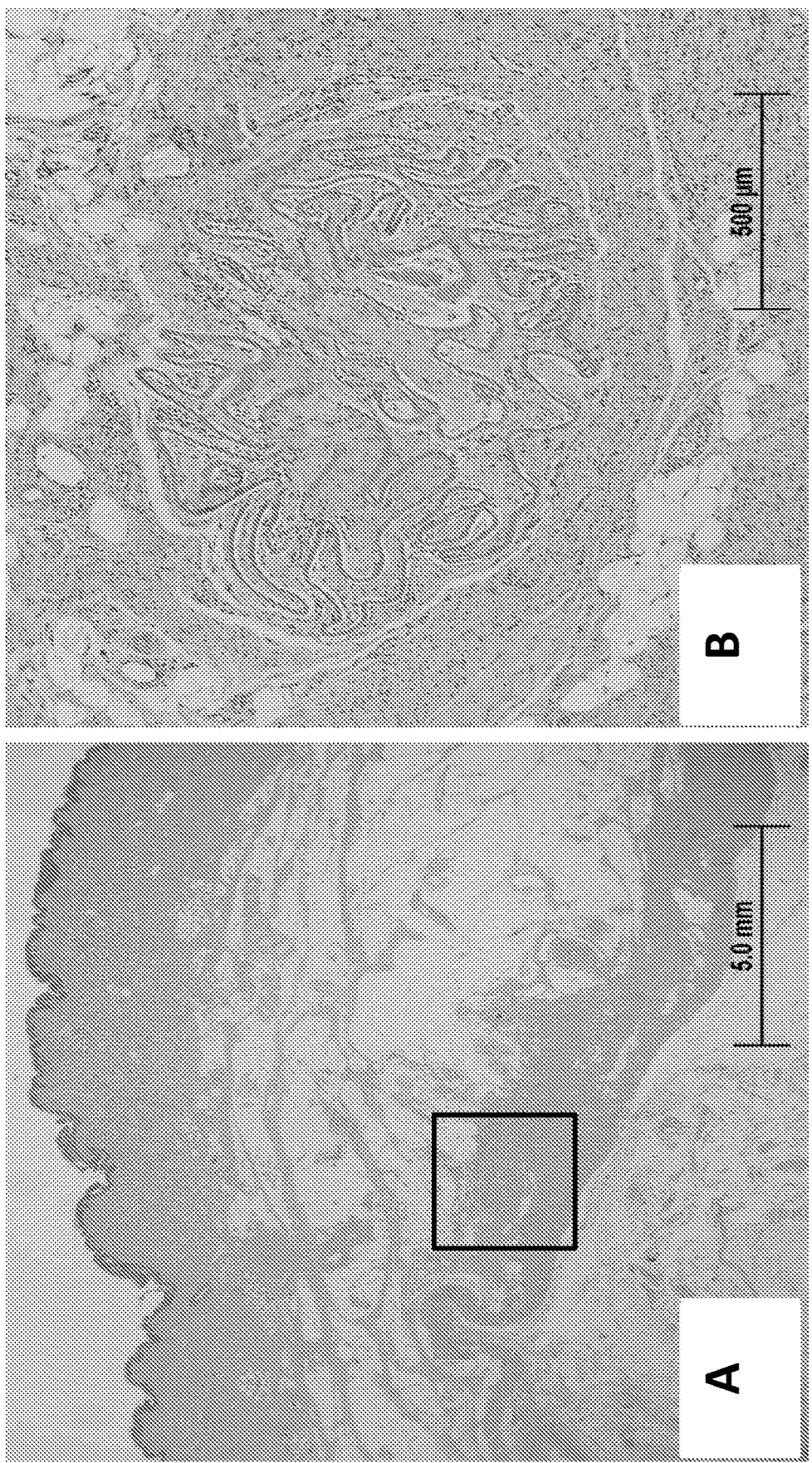
FIGS. 14A-14B: BioBridge integration in a fibrous connective tissue (3 months after implantation), low magnification (FIG. 14A) and high magnification (FIG. 14B).
Figure 15:
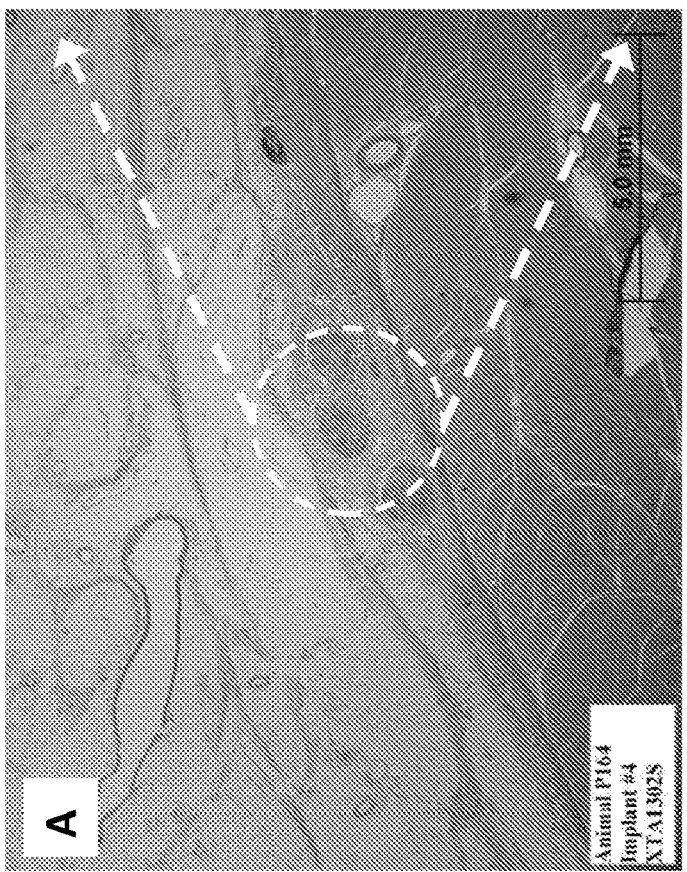
FIGS. 15A-15B: BioBridge cross section—FIG. 15A and new vessels formed along BioBridge (3 months after treatment)—FIG. 15B.
Figure 15:

These collagen fibers/fibrils provide for cell attachment, alignment, and migration (FIG. 3). To evaluate whether collagen fibrils would guide new lymphatic growth under lymphedema conditions, a large animal model using Yucatan minipigs was used. The inguinal and popliteal lymph nodes were resected and the groin area was irradiated to reproduce the conditions encountered in human patients after oncologic therapies. The status of lymphedema was assessed by detecting interstitial fluid accumulation through bioimpedance spectroscopy; the number of major lymphatic collectors by contrast-enhanced CT; and presence of lymphatic dermal backflow, in selected animal subjects, by contrast-enhanced MRI. Three months after lymph node resection, animals were subjected to a treatment surgery that involved implantation of collagen scaffolds spanning the area subjected to irradiation and depleted of lymphatics (FIG. 11). The treatment options included implantation of: (1) scaffold only, (2) scaffold enriched with VEGFC, and (3) transplantation of autologous lymph node fragments supplemented with VEGFC-enriched scaffold. The control group (4) did not receive any treatment. Analysis of bioimpedance prior to the treatment showed that 7 animals out of 16 developed chronic lymphedema. The number of lymphatic collectors, as determined by CT, correlated with bioimpedance data (FIG. 13). All animals with lymphedema in group 3 no longer had lymphedema and those in group 1 showed improvement after three months. In groups 2 and 4, lymphedema persisted in animals diagnosed with lymphedema at the pre-treatment time point, and also developed in most other animals. In groups 1 and 3, animals that were not diagnosed with lymphedema at pretreatment did not develop it. Macroscopic analysis of collectors in the implantation area after intradermal injection of methylene blue showed a number of new lymphatic collectors aligned in the direction of the implanted nanoweave thread-like scaffolds Histology in the FIG. 14 and FIG. 15 demonstrates the formation of new vasculature. FIG. 11 illustrates a plan of porcine lymphedema animal model experiment described in the Example 4. BIS is the BioImpedance Spectroscopy measurements; MRI is Magnetic Resonance Imaging; CT—contrast enhance X-ray tomography measurements. LN Res.

is the lymph node resection in the groin area of the right limb; X-ray is irradiation (15 Grey) of the groin area of the right limb after lymph node resection.

Figure 12:
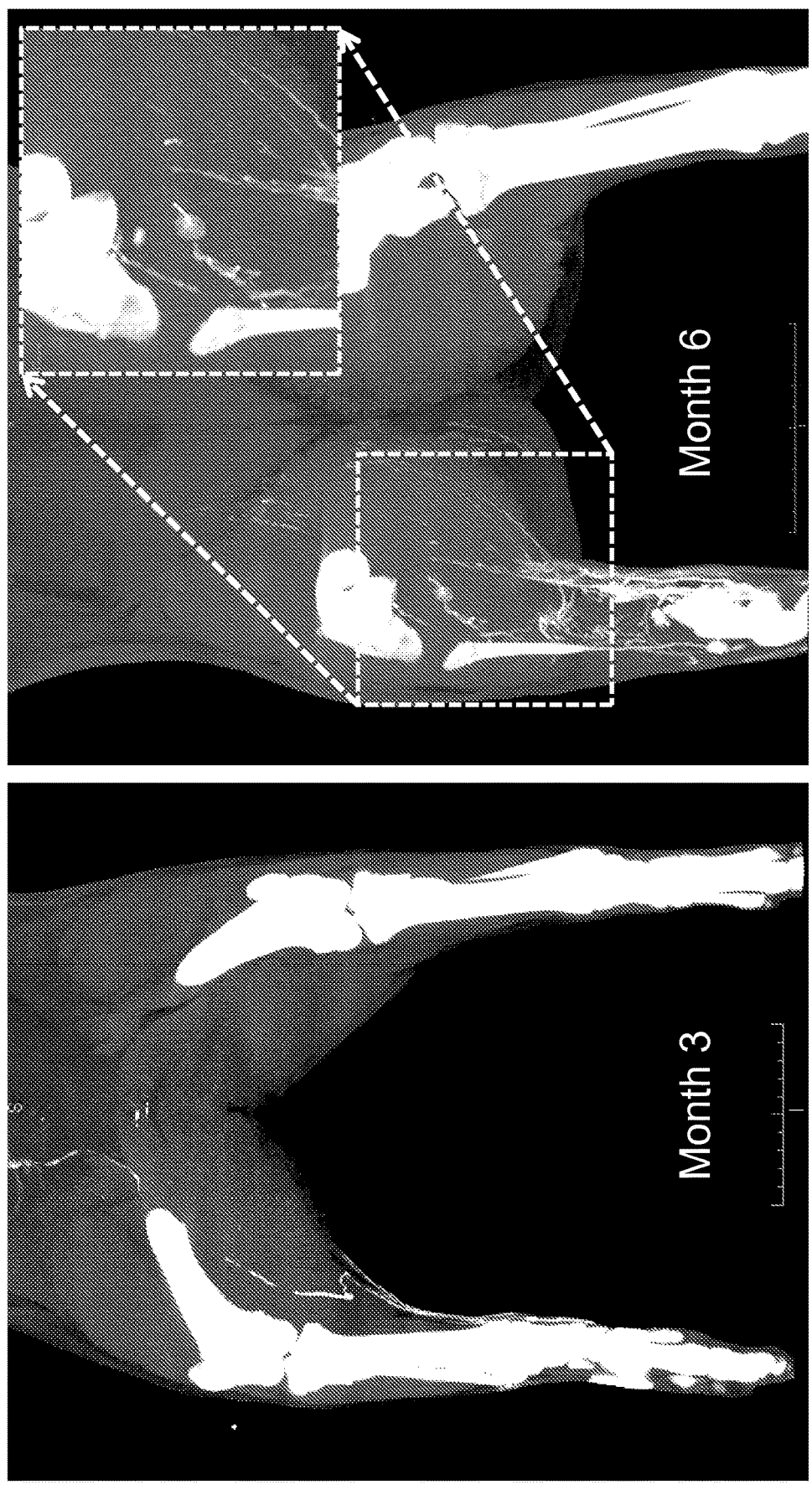
FIG. 12: The typical CT images of the pig from "Lymph Node transfer group" before (left) and after (right) treatment. "Lymph Node transfer group" is treated by the Composition included autologous lymph node fragments and BioBridge. Regeneration of the lymph node fragment is visible.

The typical CT images of the pig from "Lymph Node transfer group" before (left) and after (right) treatment are shown in FIG. 12. "Lymph Node transfer group" is treated by the Composition included autologous lymph node fragments and BioBridge. Regeneration of the lymph node fragment is visible. FIG. 13 shows the change in bioimpedance index (3 months after treatment) for each group is presented on the left and the ratio between average numbers of collectors detected by CT (3 months after treatment) for each group is presented on the right.

Figure 16:
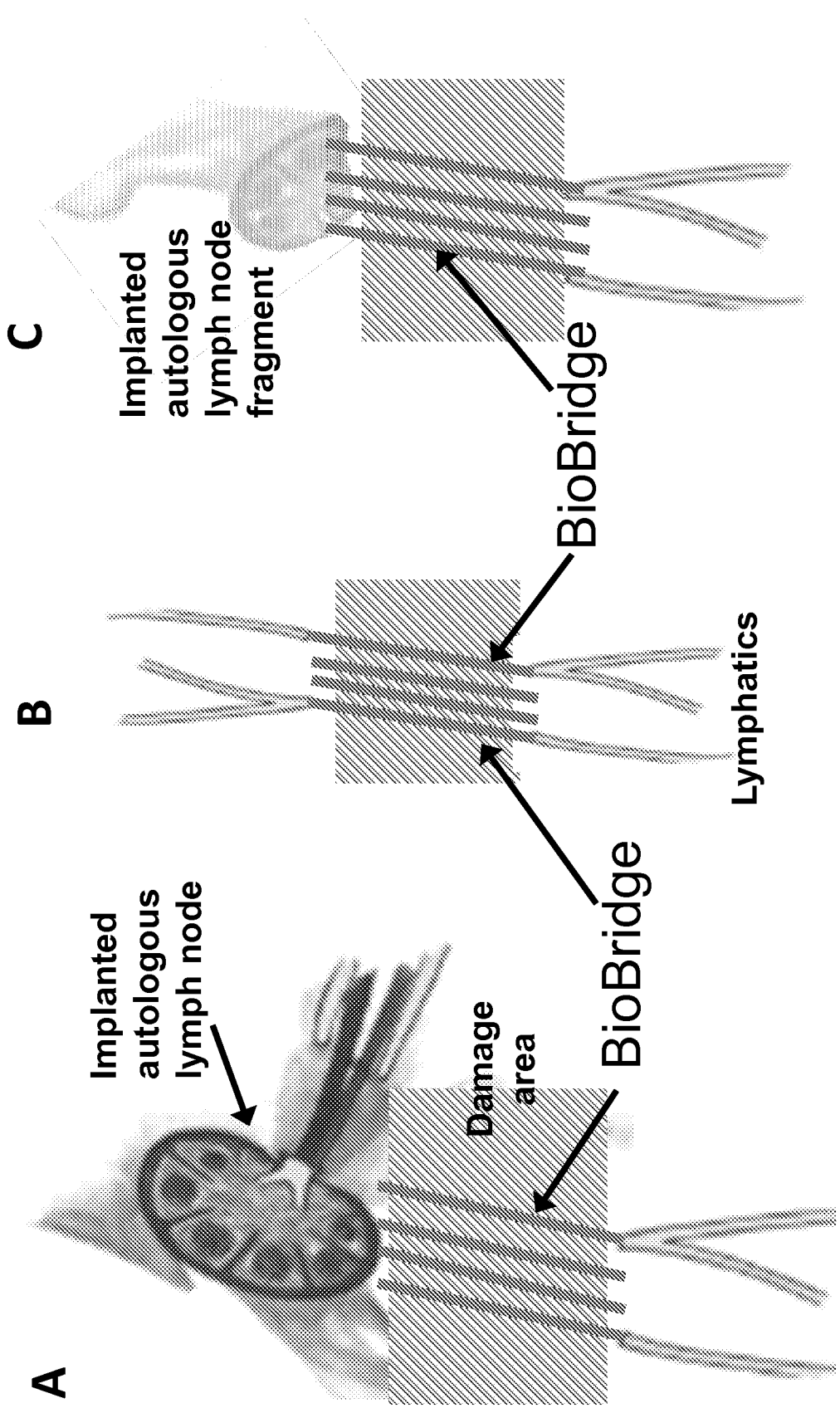
FIGS. 16A-16C.

FIG. 16 describes the preferred treatment procedures using BioBridge, BioBridge with LN, and BioBridge with lymph node fragment.

Figure 17:
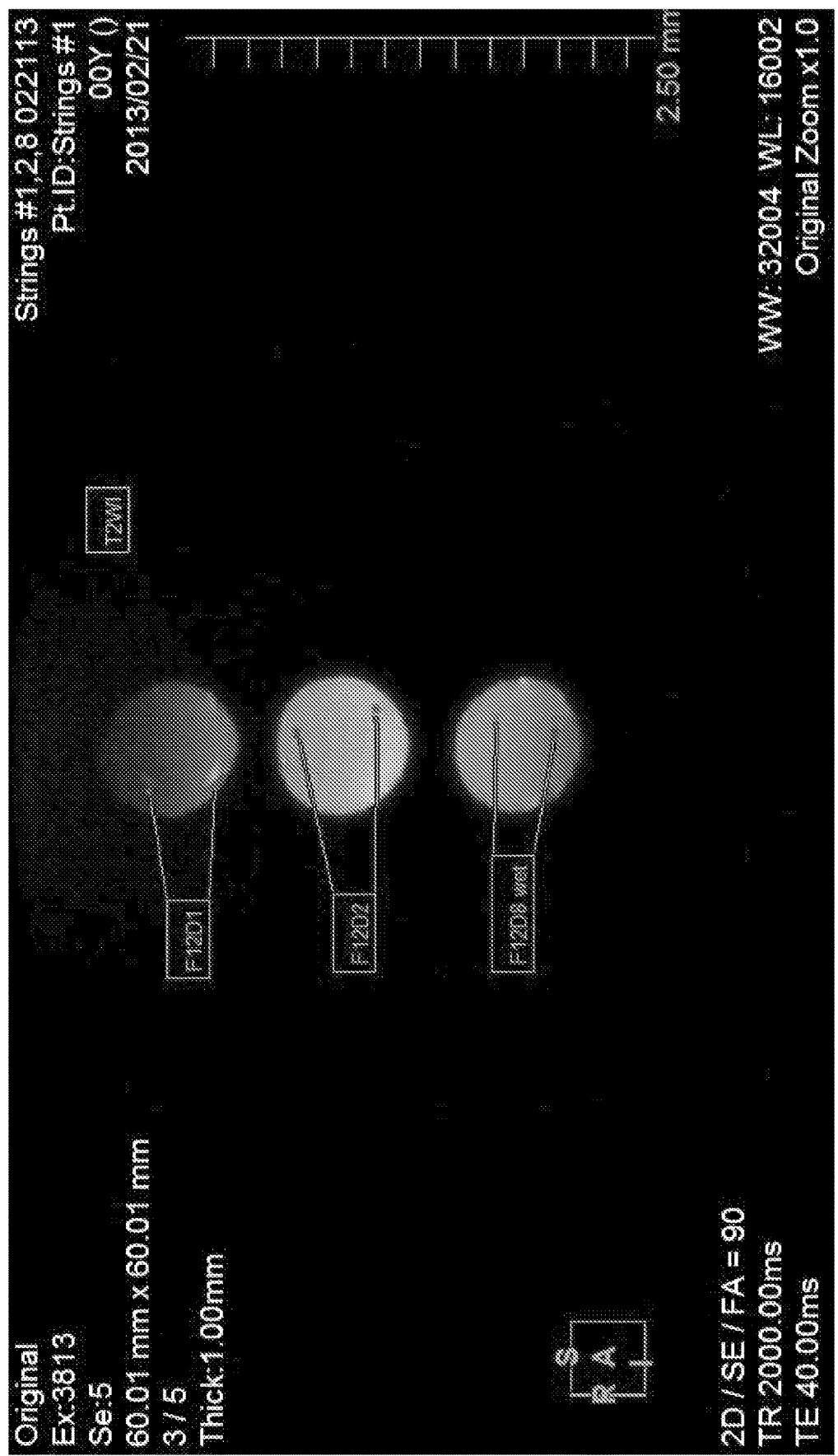
FIG. 17: 3T MRI image of the three thread-like devices (F12D1, F12D2, and F12D8). F12D2 and F12D8 have encapsulated (positive contrast) iron oxide nanoparticles with diameter about 30 nm; F12D1 has nanoparticles with negative contrast.

FIG. 17 presents the use of diagnostic markers which also can control the degradation rate of implanted scaffolds.

Figure 18:
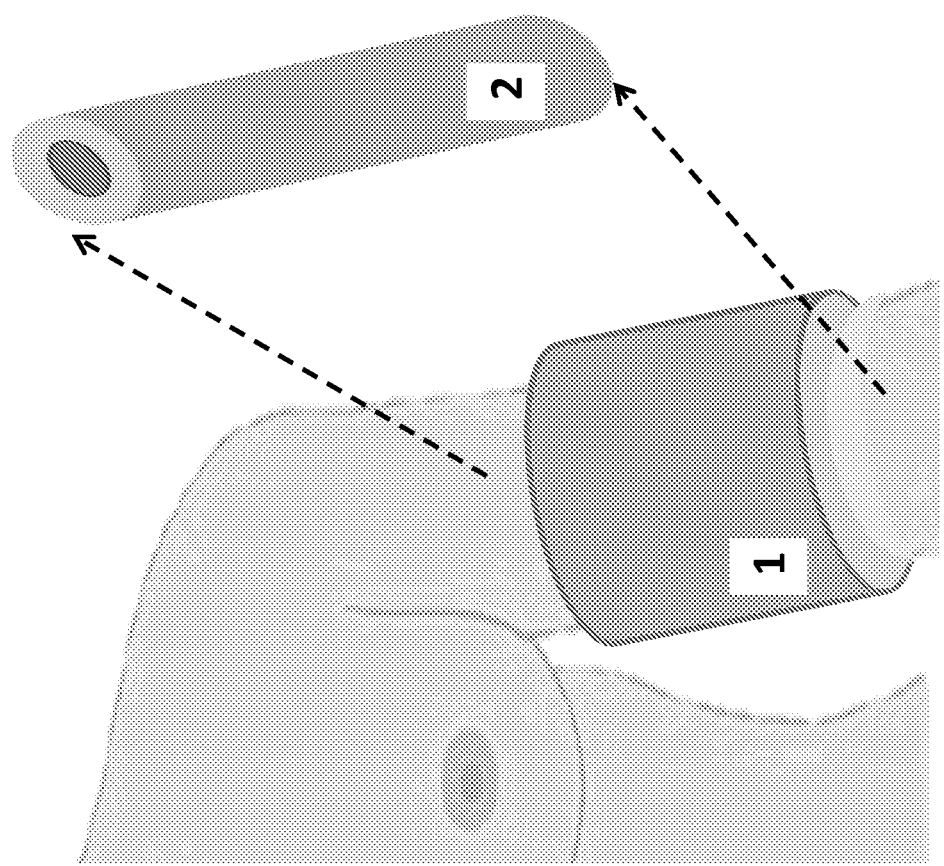
FIG. 18: Schematic diagram of the device pumping extracellular fluid through the area of disrupted lymphatics (alymphatic area); 1 is a solenoid garment—the source of the variable magnetic field inducing the electrical current in the biocompatible (biodegradable or permanent) piezoelectric tubular implant or thread-like device—2; the implant 2, which may include piezoelectric micro-pump (e.g., valveless peristaltic piezoelectric micro-pump), is bridging the area of disrupted lymphatics (alymphatic area) and pumping the extracellular fluid from the area of edema.

FIG. 18 shows a schematic diagram of an implantable device which can actively pump a fluid. This device is operated by generated external magnetic field.

While the present invention has been described in terms of specific embodiments, it is understood that variations and modifications will occur to those in the art, all of which are intended as aspects of the present invention. Accordingly, only such limitations as appear in the claims should be placed on the invention.

We claim:

1. A surgical method for reconstruction and repair of an alymphatic area comprising: implanting a composition to bridge the alymphatic area such that the composition promotes cell migration into the alymphatic area and a growth of new lymphatic or blood vessels from its periphery, wherein the composition comprises a multilumenal bundle comprised of aligned fibers or fibrils made from biocompatible and biodegradable materials, such that the multilumenal bundle bridges across the alymphatic area and induces capillary flow of extracellular fluid in the bundle, along or parallel to the bundle.

2. The method according to claim 1, wherein the composition further comprises at least one lymph node or lymph node fragment.

3. The method according to claim 1, wherein the composition further comprises at least one autologous lymph node or lymph node fragment such that the lymph node or the lymph node fragment is placed on a border of the alymphatic area.

4. The method according to claim 1, wherein the composition further comprises at least one autologous lymph node or lymph node fragment such that the lymph node or the lymph node fragment is placed in close proximity to the alymphatic area and connected to the bundle.

5. The method according to claim 1, wherein the composition includes any one or more of growth factors, cells, platelet rich plasma, peptides, drugs, silver nanowires, diagnostic markers.

6. A surgical method for reconstruction and repair of an alymphatic area comprising: implanting a composition to bridge the alymphatic area such that the composition promotes cell migration into the alymphatic area and a growth of new lymphatic or blood vessels from its periphery, wherein the composition comprises a multilumenal bundle comprised of aligned fibers or fibrils made from biocompatible and biodegradable materials, such that the multilumenal bundle bridges across the alymphatic area and induces capillary flow of extracellular fluid in the bundle, along or parallel to the bundle; and pumping, by a pump or micro-pump operated by an external magnetic field which enables pumping of interstitial fluid through the alymphatic area.

7. The method according to claim 1, wherein the bundle promotes endothelial cell survival and cell migration along the bundle and preserves endothelial cell phenotype.

8. The method according to claim 1, wherein the composition is implanted to bridge a site of disrupted lymphatic network or a gap between the healthy lymphatics or a transferred lymph node or lymph node fragments to a healthy lymphatics or a transplanted lymph node or lymph node fragments to a healthy lymphatics, such that the fibers or fibrils presented in the composition are effective to stimulate and direct the formation of new lymphatic and blood vessels at the site of the implantation.

9. The method according to claim 1, wherein the aligned fibers or fibrils are collagen-based fibrils or fibers.

10. The method according to claim 1, wherein the aligned fibers or fibrils are aligned-braided or aligned crimped collagen-based fibrils or fibers.

11. The method according to claim 1, wherein the composition includes any one or more of growth factors, cells, platelet rich plasma, peptides, drugs, silver nanowires, diagnostic markers.

12. A surgical method for reconstruction of an alymphatic area, comprising the steps:
a) forming a subcutaneous tunnel bridging the alymphatic area;
b) implanting the composition according to claim 1 in the tunnel bridging the alymphatic area;
c) securing the bundle on the border of the alymphatic area;
d) closing the tunnel.

13. The method according to claim 1, wherein the composition includes a skin flap or skin graft, wherein the skin flap or skin graft comprises at least one lymph node or lymph node fragment.

14. The method according to claim 13, wherein the composition is implanted to reduce edema or increase blood perfusion at the skin graft or skin flap, thereby improving the healing of the skin graft or skin flap.

15. The method according to claim 1, wherein the composition includes biocompatible and biodegradable materials selected from the group consisting of collagen, fibronectin, fibrin, laminin, elastin, hyaluronic acid, chitosan, silk, peptides, biodegradable block copolymers, lactide and glycolide polymers, caprolactone polymers, hydroxybutyric acids, polyanhydrides and polyesters, polyphosphazenes, polyphosphoesters, poly(ethylene glycol) (PEG) and poly(ethylene oxide) (PEO) including PEG and PEO with different end-functionalities, as well as bifunctional crosslinkers and crosslinking agents, or combinations thereof.

16. The surgical method according to claim 15, wherein the tunnel is made by one of: drilling with a catheter, or laser ablation.

* * * * *